(12) United States Patent
Miekka et al.

(10) Patent No.: US 7,848,487 B2
(45) Date of Patent: Dec. 7, 2010

(54) METHODS FOR STERILIZING BIOLOGICAL MATERIALS CONTAINING NON-AQUEOUS SOLVENTS

(75) Inventors: Shirley Miekka, Gaithersburg, MD (US); Martin J. Macphee, Montgomery Village, MD (US); William N. Drohan, Springfield, VA (US); David Mann, Gaithersburg, MD (US); Wilson Burgess, Clifton, VA (US)

(73) Assignee: Clearant, Inc., Los Angeles, CA (US)

( * ) Notice: Subject to any disclaimer, the term of this patent is extended or adjusted under 35 U.S.C. 154(b) by 207 days.

(21) Appl. No.: 12/264,106

(22) Filed: Nov. 3, 2008

(65) Prior Publication Data
US 2009/0202039 A1    Aug. 13, 2009

Related U.S. Application Data

(63) Continuation of application No. 11/812,353, filed on Jun. 18, 2007, now abandoned, which is a continuation of application No. 09/960,703, filed on Sep. 24, 2001, now abandoned.

(51) Int. Cl.
G21K 5/00    (2006.01)

(52) U.S. Cl. ........................................ 378/64

(58) Field of Classification Search .................. 378/57, 378/62, 64
See application file for complete search history.

(56) References Cited

U.S. PATENT DOCUMENTS

| | | | |
|---|---|---|---|
| RE23,195 E | 2/1950 | Brasch | |
| 2,832,689 A | 4/1958 | Proctor et al. | |
| 2,920,969 A | 1/1960 | Stoddard | |
| 2,962,380 A | 11/1960 | Wertheim | |
| 3,620,944 A | 11/1971 | Tanito et al. | |
| 3,743,480 A | 7/1973 | Falk | |
| 3,779,706 A | 12/1973 | Nablo | |
| 3,962,038 A | 6/1976 | Kawashima et al. | |
| 4,136,094 A | 1/1979 | Condie | |
| 4,251,437 A | 2/1981 | Rasmussen et al. | |
| 4,282,863 A | 8/1981 | Beigler et al. | |
| 4,330,626 A | 5/1982 | Blair et al. | |
| 4,336,247 A | 6/1982 | Eriksen | |
| 4,370,264 A | 1/1983 | Kotitschke et al. | |
| 4,409,105 A | 10/1983 | Hayashi et al. | |
| 4,472,840 A | 9/1984 | Jefferies | |
| 4,620,908 A | 11/1986 | Van Duzer | |
| 4,727,027 A | 2/1988 | Wiesehahn et al. | |
| 4,784,850 A | 11/1988 | Abraham | |

(Continued)

FOREIGN PATENT DOCUMENTS

CA    2056619    10/1991

(Continued)

*Primary Examiner*—Irakli Kiknadze
(74) *Attorney, Agent, or Firm*—Morgan Lewis & Bockius LLP

(57) ABSTRACT

Methods are disclosed for sterilizing biological materials to reduce the level of one or more active biological contaminants or pathogens therein, such as viruses, bacteria (including inter- and intracellular bacteria, such as mycoplasmas, ureaplasmas, nanobacteria, *chlamydia*, rickettsias), yeasts, molds, fungi, prions or similar agents responsible, alone or in combination, for TSEs and/or single or multicellular parasites. The methods involve sterilizing biological materials containing one or more non-aqueous solvents with irradiation.

14 Claims, 25 Drawing Sheets

U.S. PATENT DOCUMENTS

| | | | |
|---|---|---|---|
| 4,798,611 | A | 1/1989 | Freeman, Jr. |
| 4,865,602 | A | 9/1989 | Smestad et al. |
| 4,877,866 | A | 10/1989 | Rudnick et al. |
| 4,894,253 | A | 1/1990 | Heineman et al. |
| 4,931,361 | A | 6/1990 | Baldeschwieler et al. |
| 4,933,145 | A | 6/1990 | Uchida et al. |
| 4,946,648 | A | 8/1990 | Dichtelmuller et al. |
| 4,963,356 | A | 10/1990 | Calenoff et al. |
| 4,994,237 | A | 2/1991 | Login et al. |
| 5,000,951 | A | 3/1991 | Bass et al. |
| 5,002,766 | A | 3/1991 | Ransberger et al. |
| 5,012,503 | A | 4/1991 | Nambu et al. |
| 5,044,091 | A | 9/1991 | Ueda et al. |
| 5,134,295 | A | 7/1992 | Walischmiller |
| 5,185,371 | A | 2/1993 | Rubinstein |
| 5,226,065 | A | 7/1993 | Held et al. |
| 5,283,034 | A | 2/1994 | Okrongly et al. |
| 5,362,442 | A | 11/1994 | Kent |
| 5,418,130 | A | 5/1995 | Platz et al. |
| 5,460,962 | A | 10/1995 | Kemp |
| 5,510,122 | A | 4/1996 | Sreebny et al. |
| 5,548,066 | A | 8/1996 | Leneau et al. |
| 5,603,894 | A | 2/1997 | Aikus et al. |
| 5,609,864 | A | 3/1997 | Shanbrom |
| 5,637,451 | A | 6/1997 | Ben-Hur et al. |
| 5,643,464 | A | 7/1997 | Rhee et al. |
| 5,712,086 | A | 1/1998 | Horowitz et al. |
| 5,730,933 | A | 3/1998 | Peterson |
| 5,817,528 | A | 10/1998 | Bohm et al. |
| 5,837,313 | A | 11/1998 | Ding et al. |
| 5,856,172 | A | 1/1999 | Greenwood et al. |
| 5,881,534 | A | 3/1999 | Ahlqvist et al. |
| 5,911,951 | A | 6/1999 | Girardot et al. |
| 5,958,669 | A | 9/1999 | Ogle et al. |
| 5,965,349 | A | 10/1999 | Lin et al. |
| 5,981,163 | A | 11/1999 | Horowitz et al. |
| 5,986,168 | A | 11/1999 | Noishiki |
| 5,989,498 | A | 11/1999 | Odland |
| 6,010,719 | A | 1/2000 | Remon et al. |
| 6,046,024 | A | 4/2000 | Burton et al. |
| 6,049,025 | A | 4/2000 | Stone et al. |
| 6,060,233 | A | 5/2000 | Wiggins |
| 6,066,626 | A | 5/2000 | Yew et al. |
| 6,087,141 | A | 7/2000 | Margolis-Nunno et al. |
| 6,120,592 | A | 9/2000 | Brault et al. |
| 6,139,746 | A | 10/2000 | Kopf |
| 6,159,490 | A | 12/2000 | Deghenghi |
| 6,171,549 | B1 | 1/2001 | Kent |
| 6,187,572 | B1 | 2/2001 | Platz et al. |
| 6,190,855 | B1 | 2/2001 | Herman et al. |
| 6,197,207 | B1 | 3/2001 | Chapman et al. |
| 6,203,544 | B1 | 3/2001 | Gotzen |
| 6,214,534 | B1 | 4/2001 | Horowitz et al. |
| 6,235,508 | B1 | 5/2001 | Sowemimo-Coker et al. |
| 6,258,821 | B1 | 7/2001 | Stogniew et al. |
| 6,312,931 | B1 | 11/2001 | O'Dwyer et al. |
| 6,346,216 | B1 | 2/2002 | Kent |
| 6,358,284 | B1 | 3/2002 | Fearnot et al. |
| 6,375,989 | B1 | 4/2002 | Badylak et al. |
| 6,383,732 | B1 | 5/2002 | Stone |
| 6,383,810 | B2 | 5/2002 | Fike et al. |
| 6,384,419 | B1 | 5/2002 | Purtle |
| 6,461,630 | B1 | 10/2002 | Tucker et al. |
| 6,485,723 | B1 | 11/2002 | Badylak et al. |
| 2001/0049141 | A1 | 12/2001 | Fike et al. |
| 2002/0064807 | A1 | 5/2002 | Badylak et al. |
| 2002/0106394 | A1 | 8/2002 | Tucker et al. |
| 2002/0188319 | A1 | 12/2002 | Morris et al. |
| 2003/0068815 | A1 | 4/2003 | Stone et al. |

FOREIGN PATENT DOCUMENTS

| | | |
|---|---|---|
| DE | 38 17 603 | 11/1989 |
| DE | 280466 | 7/1990 |
| EP | 310 316 | 4/1989 |
| EP | 334 679 | 9/1989 |
| EP | 919 918 | 6/1999 |
| EP | 0808167 | 6/2002 |
| EP | 0820301 | 7/2002 |
| JP | 408098688 A | 4/1996 |
| JP | 11-216147 | 8/1999 |
| SU | 1321420 | 7/1987 |
| WO | WO 88/06043 | 8/1988 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 00/52031 | 9/2000 |
| WO | WO 01/08611 | 2/2001 |
| WO | WO 01/12318 | 2/2001 |
| WO | WO 01/32107 | 5/2001 |
| WO | WO 01/32110 | 5/2001 |
| WO | WO 01/45720 | 6/2001 |
| WO | WO 01/49219 | 7/2001 |
| WO | WO 01/72233 | 10/2001 |
| WO | WO 01/72244 | 10/2001 |
| WO | WO 01/91818 | 12/2001 |

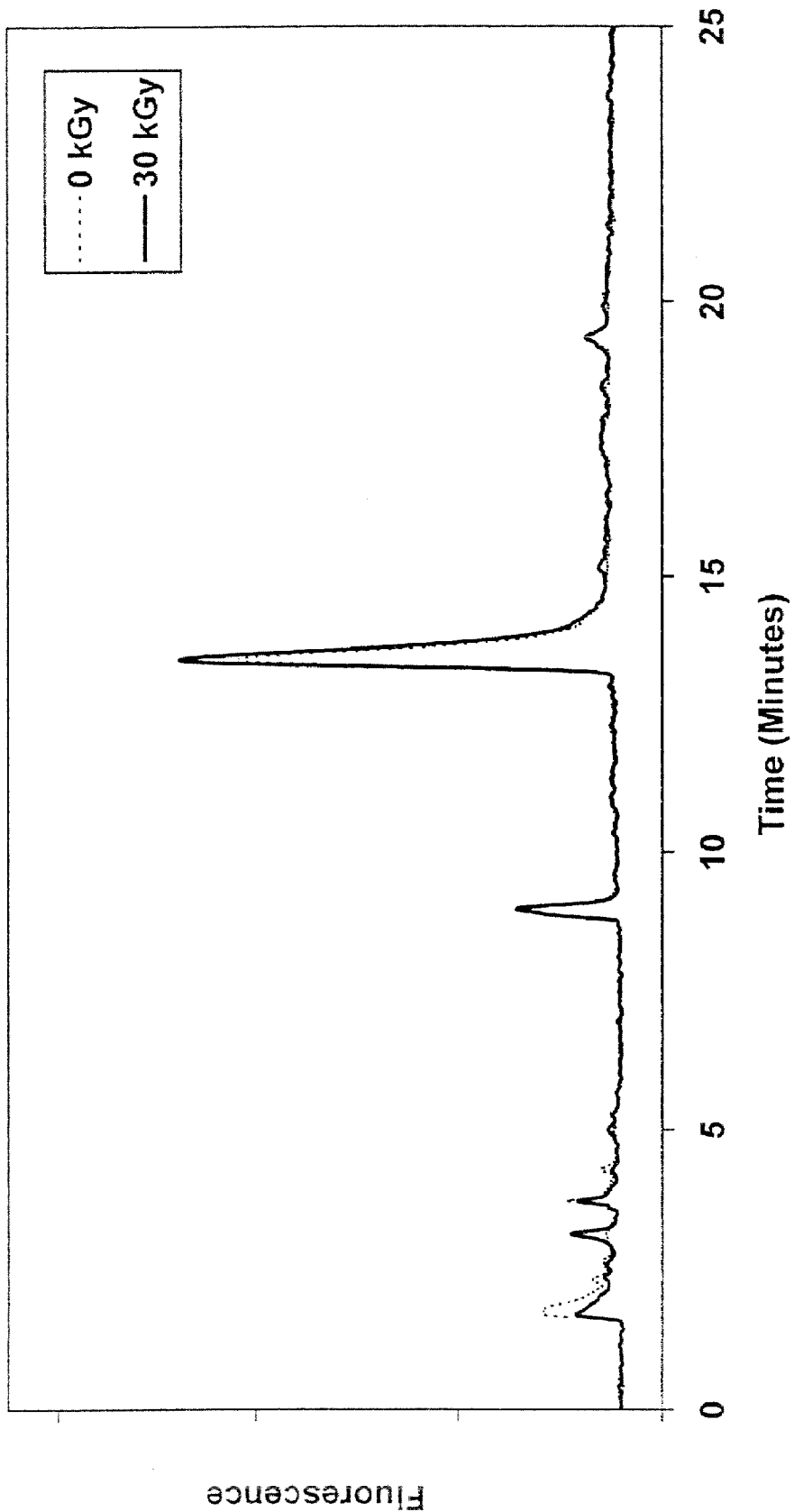

METHODS FOR STERILIZING BIOLOGICAL MATERIALS CONTAINING NON-AQUEOUS SOLVENTS

This is a continuation application of U.S. patent application Ser. No. 11/812,353, filed Jun. 18, 2007, now abandoned which is a continuation application of U.S. application Ser. No. 09/960,703, filed Sep. 24, 2001, now abandoned both of which are herein incorporated by reference in their entireties.

BACKGROUND OF THE INVENTION

1. Field of the Invention

The present invention relates to methods for sterilizing biological materials to reduce the level of one or more active biological contaminants or pathogens therein, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. The present invention particularly relates to methods of sterilizing biological materials containing one or more non-aqueous solvents with irradiation.

2. Background of the Related Art

Many biological materials that are prepared for human, veterinary, diagnostic and/or experimental use may contain unwanted and potentially dangerous biological contaminants or pathogens, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. Consequently, it is of utmost importance that any biological contaminant or pathogen in the biological material be inactivated before the product is used. This is especially critical when the material is to be administered directly to a patient, for example in blood transfusions, blood factor replacement therapy, organ transplants and other forms of human therapy corrected or treated by intravenous, intramuscular or other forms of injection or introduction. This is also critical for the various biological materials that are prepared in media or via culture of cells or recombinant cells which contain various types of plasma and/or plasma derivatives or other biologic materials and which may be subject to mycoplasma, prion, bacterial, viral and other biological contaminants or pathogens.

Most procedures for producing biological materials have involved methods that screen or test the biological materials for one or more particular biological contaminants or pathogens rather than removal or inactivation of the contaminant(s) or pathogen(s) from the material. Materials that test positive for a biological contaminant or pathogen are merely not used. Examples of screening procedures include the testing for a particular virus in human blood from blood donors. Such procedures, however, are not always reliable and are not able to detect the presence of certain viruses, particularly in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the material is contaminated. Moreover, to date, there is no reliable test or assay for identifying prions within a biological material that is suitable for screening out potential donors or infected material. This serves to heighten the need for an effective means of destroying prions within a biological material, while still retaining the desired activity of that material. Therefore, it would be desirable to apply techniques that would kill or inactivate contaminants or pathogens during and/or after manufacturing the biological material.

The importance of these techniques is apparent regardless of the source of the biological material. All living cells and multi-cellular organisms can be infected with viruses and other pathogens. Thus the products of unicellular natural or recombinant organisms or tissues carry a risk of pathogen contamination. In addition to the risk that the producing cells or cell cultures may be infected, the processing of these and other biological materials creates opportunities for environmental contamination. The risks of infection are more apparent for multicellular natural and recombinant organisms, such as transgenic animals. Interestingly, even products from species as different from humans as transgenic plants carry risks, both due to processing contamination as described above, and from environmental contamination in the growing facilities, which may be contaminated by pathogens from the environment or infected organisms that co-inhabit the facility along with the desired plants. For example, a crop of transgenic corn grown out of doors, could be expected to be exposed to rodents such as mice during the growing season. Mice can harbour serious human pathogens such as the frequently fatal Hanta virus. Since these animals would be undetectable in the growing crop, viruses shed by the animals could be carried into the transgenic material at harvest. Indeed, such rodents are notoriously difficult to control, and may gain access to a crop during sowing, growth, harvest or storage. Likewise, contamination from overflying or perching birds has to potential to transmit such serious pathogens as the causative agent for psittacosis. Thus any biological material, regardless of its source, may harbour serious pathogens that must be removed or inactivated prior to the administration of the material to a recipient.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used. In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses' diminutive size is associated with a small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses of concern for both human and animal-derived biological materials, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focussed on methods to remove or inactivate contaminants in the products. Such methods include heat treating, filtration and the addition of chemical inactivants or sensitizers to the product.

According to current standards of the U.S. Food and Drug Administration, heat treatment of biological materials may require healing to approximately 60° C. for a minimum of 10 hours, which can be damaging to sensitive biological materials. Indeed, heat inactivation can destroy 50% or more of the biological activity of certain biological materials.

Filtration involves filtering the product in order to physically remove contaminants. Unfortunately, this method may also remove products that have a high molecular weight. Further, in certain cases, small viruses may not be removed by the filter.

The procedure of chemical sensitization involves the addition of noxious agents which bind to the DNA/RNA of the virus and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer is washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly et al., "Is There Life After Irradiation? Part 2," *BioPharm* July-August, 1993, and Leitman, "Use of Blood Cell Irradiation in the Prevention of Post Transfusion Graft-vs-HostDisease," *Transfusion Science* 10:219-239 (1989)). The published literature in this area, however, teaches that gamma radiation can be damaging to radiation sensitive products, such as blood, blood products, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". Unfortunately, many sensitive biological materials, such as monoclonal antibodies (Mab), may lose viability and activity if subjected to freezing for irradiation purposes and then thawing prior to administration to a patient.

In view of the difficulties discussed above, there remains a need for methods of sterilizing biological materials that are effective for reducing the level of active biological contaminants or pathogens without an adverse effect on the material.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

Accordingly, it is an object of the present invention to provide methods of sterilizing biological materials by reducing the level of active biological contaminants or pathogens without adversely effecting the material. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for sterilizing a biological material that is sensitive to radiation and contains a non-aqueous solvent comprising irradiating the biological material with radiation for a time effective to sterilize the material at a rate effective to sterilize the material and to protect the material from radiation.

Another embodiment of the present invention is directed to a method for sterilizing a biological material that is sensitive to radiation and contains a non-aqueous solvent comprising: (i) adding to a biological material at least one stabilizer in an amount effective to protect the biological material from radiation; and (ii) irradiating the biological material with radiation at an effective rate for a time effective to sterilize the material.

Another embodiment of the present invention is directed to a method for sterilizing a biological material that is sensitive to radiation and contains a non-aqueous solvent comprising: (i) reducing the residual solvent content of a biological material to a level effective to protect the biological material from radiation; and (ii) irradiating the biological material with radiation at an effective rate for a time effective to sterilize the biological material.

Another embodiment of the present invention is directed to a method for sterilizing a biological material that is sensitive to radiation and contains a non-aqueous solvent comprising: (i) reducing the temperature of a biological material to a level effective to protect the biological material from radiation; and (ii) irradiating the biological material with radiation at an effective rate for a time effective to sterilize the biological material.

Another embodiment of the present invention is directed to a method for sterilizing a biological material that is sensitive to radiation and contains a non-aqueous solvent comprising: (i) applying to the biological material a stabilizing process selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing process and the rate of irradiation are together effective to protect the biological material from radiation.

Another embodiment of the present invention is directed to a method for sterilizing a biological material that is sensitive to radiation and contains a non-aqueous solvent comprising: (i) applying to the biological material at least two stabilizing processes selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing processes may be performed in any order and are together effective to protect the biological material from radiation.

The invention also provides a composition comprising a biological material and a non-aqueous solvent in an amount effective to preserve the preparation for its intended use following sterilization with radiation.

The invention also provides a composition comprising at least one biological material, a least one non-aqueous solvent and at least one stabilizer, wherein the non-aqueous solvent and stabilizer are together present in an amount effective to preserve the material for its intended use following sterilization with radiation.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIGS. 4(a)-4(d) show the effects of porcine heart valves gamma irradiated in the presence of polypropylene glycol 400 (PPG400) and, optionally, a scavenger.

DETAILED DESCRIPTION OF PREFERRED EMBODIMENTS

A. Definitions

Figure 1:
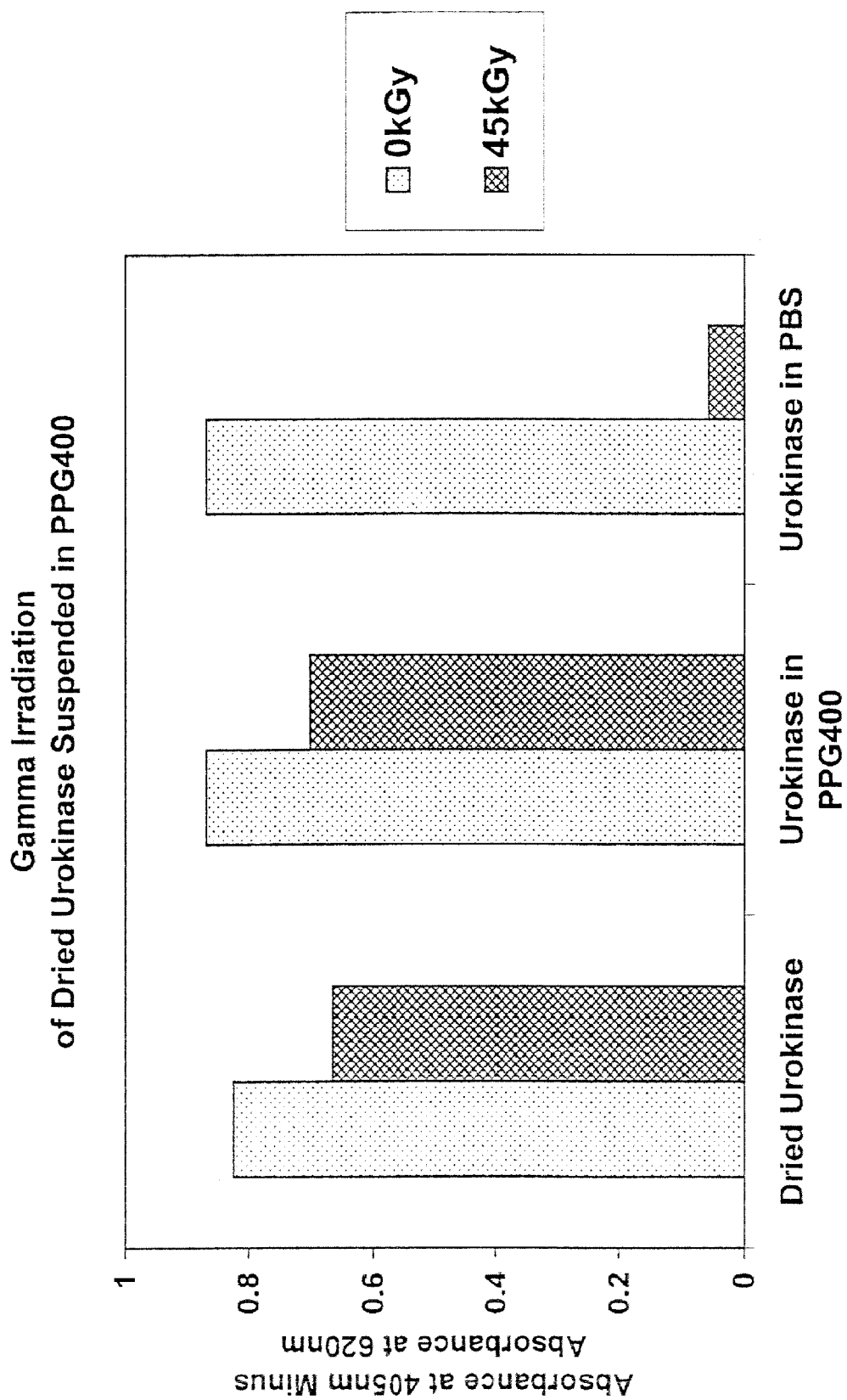
FIG. 1 is a graph showing the effect of gamma radiation on dried urokinase suspended in polypropylene glycol (PPG) 400 or phosphate buffered saline (PBS).

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "sterilize" is intended to mean a reduction in the level of at least one active biological contaminant or pathogen found in the biological material being treated according to the present invention.

As used herein, the term "biological material" is intended to mean any substance derived or obtained from a living organism. Illustrative examples of biological materials include, but are not limited to, the following: cells; tissues; blood or blood components; proteins, including recombinant and transgenic proteins, and proteinaceous materials; enzymes, including digestive enzymes, such as trypsin, chymotrypsin, alpha-galactosidase and iduronodate-2-sulfatase; immunoglobulins, including mono and polyimmunoglobulins; botanicals; food and the like. Preferred examples of biological materials include, but are not limited to, the following: ligaments; tendons; nerves; bone, including demineralized bone matrix, grafts, joints, femurs, femoral heads, etc.; teeth; skin grafts; bone marrow, including bone marrow cell suspensions, whole or processed; heart valves; cartilage; corneas; arteries and veins; organs, including organs for transplantation, such as hearts, livers, lungs, kidneys, intestines, pancreas, limbs and digits; lipids; carbohydrates; collagen, including native, afibrillar, atelomeric, soluble and insoluble, recombinant and transgenic, both native sequence and modified; chitin and its derivatives, including NO-carboxy chitosan (NOCC); stem cells, islet of Langerhans cells and other cells for transplantation, including genetically altered cells; red blood cells; white blood cells, including monocytes; and platelets.

As used herein, the term "non-aqueous solvent" is intended to mean any liquid other than water in which a biological material may be dissolved or suspended and includes both inorganic solvents and, more preferably, organic solvents. Illustrative examples of suitable non-aqueous solvents include, but are not limited to, the following: alkanes and cycloalkanes, such as pentane, 2-methylbutane (isopentane), heptane, hexane, cyclopentane and cyclohexane; alcohols, such as methanol, ethanol, 2-methoxyethanol, isopropanol, n-butanol, t-butyl alcohol, and octanol; esters, such as ethyl acetate, 2-methoxyethyl acetate, butyl acetate and benzyl benzoate; aromatics, such as benzene, toluene, pyridine, xylene; ethers, such as diethyl ether, 2-ethoxyethyl ether, ethylene glycol dimethyl ether and methyl t-butyl ether; aldehydes, such as formaldehyde and glutaraldehyde; ketones, such as acetone and 3-pentanone (diethyl ketone); glycols, including both monomeric glycols, such as ethylene glycol and propylene glycol, and polymeric glycols, such as polyethylene glycol (PEG) and polypropylene glycol (PPG), e.g., PPG 400, PPG 1200 and PPG 2000; acids and acid anhydrides, such as formic acid, acetic acid, trifluoroacetic acid, phosphoric acid and acetic anhydride; oils, such as cottonseed oil, peanut oil, culture media, polyethylene glycol, poppyseed oil, safflower oil, sesame oil, soybean oil and vegetable oil; amines and amides, such as piperidine, N,N-dimethylacetamide and N,N-dimethylformamide; dimethylsulfoxide (DMSO); nitriles, such as benzonitrile and acetonitrile; hydrazine; detergents, such as polyoxyethylenesorbitan monolaurate (Tween 20) and monooleate (Tween 80), Triton and sodium dodecyl sulfate; carbon disulfide; halogenated solvents, such as dichloromethane, chloroform, carbon tetrachloride, 1,2-dichlorobenzene, 1,2-dichloroethane, tetrachloroethylene and 1-chlorobutane; furans, such as tetrahydrofuran; oxanes, such as 1,4-dioxane; and glycerin/glycerol. Particularly preferred examples of suitable non-aqueous solvents include non-aqueous solvents which also function as stabilizers, such as ethanol and acetone.

As used herein, the term "biological contaminant or pathogen" is intended to mean a biological contaminant or pathogen that, upon direct or indirect contact with a biological material, may have a deleterious effect on the biological material or upon a recipient thereof. Such other biological contaminants or pathogens include the various viruses, bacteria (including inter- and intracellular bacteria, such as mycoplasmas, ureaplasmas, nanobacteria, *chlamydia*, rickettsias), yeasts, molds, fungi, prions or similar agents responsible, alone or in combination, for TSEs and/or single or multicellular parasites known to those of skill in the art to generally be found in or infect biological materials. Examples of other biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C and variants thereof), pox viruses, toga viruses, Ebstein-Barr viruses and parvoviruses; bacteria, such as *Escherichia, Bacillus, Campylobacter, Streptococcus* and *Staphatococcus*; nanobacteria; parasites, such as *Trypanosoma* and malarial parasites, including *Plasmodium* species; yeasts; molds; fungi; mycoplasmas and ureaplasmas; *chlamydia*; rickettsias, such as *Coxiella burnetii*; and prions and similar agents responsible, alone or in combination, for one or more of the disease states known as transmissible spongiform encephalopathies (TSEs) in mammals, such as scrapie, transmissible mink encephalopathy, chronic wasting disease (generally observed in mule deer and elk), feline spongiform encephalopathy, bovine spongiform encephalopathy (mad cow disease), Creutzfeld-Jakob disease (including variant CJD), Fatal Familial Insomnia, Gerstmann-Straeussler-Scheinker syndrome, kuru and Alpers syndrome. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the biological material and/or a recipient thereof.

As used herein, the term "blood components" is intended to mean one or more of the components that may be separated from whole blood and include, but are not limited to, the following: cellular blood components, such as red blood cells, white blood cells and platelets; blood proteins, such as blood clotting factors, enzymes, albumin, plasminogen, fibrinogen and immunoglobulins; and liquid blood components, such as plasma, plasma protein fraction (PPF), cryoprecipitate, plasma fractions and plasma-containing compositions.

As used herein, the term "cellular blood component" is intended to mean one or more of the components of whole blood that comprises cells, such as red blood cells, white blood cells, stem cells and platelets.

As used herein, the term "blood protein" is intended to mean one or more of the proteins that are normally found in whole blood. Illustrative examples of blood proteins found in mammals, including humans, include, but are not limited to, the following: coagulation proteins, both vitamin K-dependent, such as Factor VII and Factor IX, and non-vitamin K-dependent, such as Factor VIII and von Willebrands factor; albumin; lipoproteins, including high density lipoproteins and low density lipoproteins; complement proteins; globulins, such as immunoglobulins IgA, IgM, IgG and IgE; and the like. A preferred group of blood proteins includes Factor I (fibrinogen), Factor II (prothrombin), Factor III (tissue factor), Factor V (proaccelerin), Factor VI (accelerin), Factor VII (proconvertin, serum prothrombin conversion), Factor VIII (antihemophiliac factor A), Factor IX (antihemophiliac factor B), Factor X (Stuart-Prower factor), Factor XI (plasma thromboplastin antecedent), Factor XII (Hageman factor), Factor XIII (protransglutamidase), von Willebrands factor (vWF), Factor Ia, Factor IIa, Factor IIIa, Factor Va, Factor VIa, Factor VIIa, Factor VIIIa, Factor IXa, Factor Xa, Factor XIa, Factor XIIa and Factor XIIIa. Another preferred group of blood proteins includes proteins found inside red blood cells, such as hemoglobin and various growth factors, and derivatives of these proteins. Yet another preferred group of blood proteins include proteins found in commercially available plasma protein fraction products, such as Plasma-Plex® (Centeon/Aventis Behring), Protenate® (Baxter Laboratories), Plasmanate® (Bayer Biological) and Plasmatein® (Alpha Therapeutic).

As used herein, the term "liquid blood component" is intended to mean one or more of the fluid, non-cellular components of whole blood, such as plasma (the fluid, non-cellular portion of the whole blood of humans or animals as found prior to coagulation) and serum (the fluid, non-cellular portion of the whole blood of humans or animals as found after coagulation).

As used herein, the term "a biologically compatible solution" is intended to mean a solution to which a biological material may be exposed, such as by being suspended or dissolved therein, and remain viable, i.e., retain its essential biological and physiological characteristics.

As used herein, the term "a biologically compatible buffered solution" is intended to mean a biologically compatible solution having a pH and osmotic properties (e.g., tonicity, osmolality and/or oncotic pressure) suitable for maintaining the integrity of the material(s) therein. Suitable biologically compatible buffered solutions typically have a pH between 4 and 8.5 and are isotonic or only moderately hypotonic or hypertonic. Biologically compatible buffered solutions are known and readily available to those of skill in the art.

As used herein, the term "stabilizer" is intended to mean a compound or material that reduces damage to the biological material being irradiated to a level that is insufficient to preclude the safe and effective use of the material. Illustrative examples of stabilizers include, but are not limited to, the following: antioxidants; free radical scavengers, including spin traps, such as tert-butyl-nitrosobutane (tNB), α-phenyl-tert-butylnitrone (PBN), 5,5-dimethylpyrroline-N-oxide (DMPO), tert-butylnitrosobenzene (BNB), α-(4-pyridyl-1-oxide)-N-tert-butylnitrone (4-POBN) and 3,5-dibromo-4-nitroso-benzenesulphonic acid (DBNBS); combination stabilizers, i.e., stabilizers which are effective at quenching both Type I and Type II photodynamic reactions; and ligands, such as heparin, that stabilize the molecules to which they bind. Preferred examples of stabilizers include, but are not limited to, the following: ethanol; acetone; fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tatranor-dihydrolipoic acid, furan fatty acids, oleic and linoleic and palmitic acids and their salts and derivatives; flavonoids, phenylpropanoids, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalose; amino acids and derivatives thereof, such as histidine, N-acetylcysteine (NAC), glutamic acid, tryptophan, sodium caprylate, N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and reduced glutathione and cysteine; trace elements, such as selenium; vitamins, such as vitamin A, vitamin C (including its derivatives and salts such as sodium ascorbate and palmitoyl ascorbic acid) and vitamin E (and its derivatives and salts such as tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin: tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins and peptides, such as glycylglycine and carnosine, in which each amino acid may be in its D or L form; diosmin; pupurogalin; gallic acid and its derivatives including but not limited to propyl gallate, sodium formaldehyde sulfoxylate and silymarin. Particularly preferred examples include single stabilizers or combinations of stabilizers that are effective at quenching both Type I and Type II photodynamic reactions and volatile stabilizers, which can be applied as a gas and/or easily removed by evaporation, low pressure and similar methods. Such individual or combinations of stabilizers are referred to herein as "combination stabilizers".

As used herein, the term "residual solvent content" is intended to mean the amount or proportion of freely-available liquid in the biological material. Freely-available liquid means the liquid, such as water or an organic solvent (e.g., ethanol, isopropanol, acetone, polyethylene glycol, etc.), present in the biological material being sterilized that is not bound to or complexed with one or more of the non-liquid components of the material. Freely-available liquid includes intracellular water. The residual solvent contents related as water referenced herein refer to levels determined by the FDA approved, modified Karl Fischer method (Meyer and Boyd, *Analytical Chem.*, 31:215-219, 1959; May, et al., *J. Biol. Standardization*, 10:249-259, 1982; Centers for Biologics Evaluation and Research, FDA, Docket No. 89D-0140, 83-93; 1990) or by near infrared spectroscopy. Quantitation of the residual levels of other solvents may be determined by means well known in the art, depending upon which solvent is employed. The proportion of residual solvent to solute may also be considered to be a reflection of the concentration of the solute within the solvent. When so considered, the greater the concentration of the solute, the lower the amount of residual solvent.

As used herein, the term "sensitizer" is intended to mean a substance that selectively targets viral, bacterial, prion and/or parasitic contaminants, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphorins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide. In addition, atoms which bind to prions, and thereby increase their sensitivity to inactivation by radiation, may also be used. An illustrative example of such an atom would be the Copper ion, which binds to the prior protein and, with a Z number higher than the other atoms in the protein, increases the probability that the prion protein will absorb energy during irradiation, particularly gamma irradiation.

As used herein, the term "proteinaceous material" is intended to mean any material derived or obtained from a living organism that comprises at least one protein or peptide. A proteinaceous material may be a naturally occurring material, either in its native state or following processing/purification and/or derivatization, or an artificially produced material, produced by chemical synthesis or recombinant/transgenic technology and, optionally, process/purified and/or derivatized. Illustrative examples of proteinaceous materials include, but are not limited to, the following: proteins and peptides produced from cell culture; milk and other dairy products; ascites; hormones; growth factors; materials, including pharmaceuticals, extracted or isolated from animal tissue, such as heparin and insulin, or plant matter; plasma, including fresh, frozen and freeze-dried, and plasma protein fraction; fibrinogen and derivatives thereof, fibrin, fibrin I, fibrin II, soluble fibrin and fibrin monomer, and/or fibrin sealant products; whole blood; protein C; protein S; alpha-1 anti-trypsin (alpha-1 protease inhibitor); butyl-cholinesterase; anticoagulants, such as coumarin drugs (warfarin); streptokinase; tissue plasminogen activator (tPA); erythropoietin (EPO); urokinase; neupogen; anti-thrombin-3; alpha-glucosidase: (fetal) bovine serum/horse serum; meat; immunoglobulins, including anti-sera, monoclonal antibodies, polyclonal antibodies and genetically engineered or produced antibodies; albumin; alpha-globulins; beta-globulins; gamma-globulins; coagulation proteins; complement proteins; and interferons.

As used herein, the term "radiation" is intended to mean radiation of sufficient energy to sterilize at least some component of the irradiated biological material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves. Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As used herein, the term "to protect" is intended to mean to reduce any damage to the biological material being irradiated, that would otherwise result from the irradiation of that material, to a level that is insufficient to preclude the safe and effective use of the material following irradiation. In other words, a substance or process "protects" a biological material from radiation if the presence of that substance or carrying out that process results in less damage to the material from irradiation than in the absence of that substance or process. Thus, biological material may be used safely and effectively after irradiation in the presence of a substance or following performance of a process that "protects" the material, but could not be used safely and effectively after irradiation under identical conditions but in the absence of that substance or the performance of that process.

As used herein, an "acceptable level" of damage may vary depending upon certain features of the particular method(s) of the present invention being employed, such as the nature and characteristics of the particular biological material and/or non-aqueous solvent(s) being used, and/or the intended use of the biological material being irradiated, and can be determined empirically by one skilled in the art. An "unacceptable level" of damage would therefore be a level of damage that would preclude the safe and effective use of the biological material being sterilized. The particular level of damage in a given biological material may be determined using any of the methods and techniques known to one skilled in the art.

B. Particularly Preferred Embodiments

A first preferred embodiment of the present invention is directed to a method for sterilizing a biological material that is sensitive to radiation and contains a non-aqueous solvent comprising irradiating the biological material with radiation for a time effective to sterilize the material at a rate effective to sterilize the material and to protect the material from radiation.

Another preferred embodiment of the present invention is directed to a method for sterilizing a biological material that is sensitive to radiation and contains a non-aqueous solvent comprising: (i) adding to a biological material at least one stabilizer in an amount effective to protect the biological material from radiation; and (ii) irradiating the biological material with radiation at an effective rate for a time effective to sterilize the material.

Another preferred embodiment of the present invention is directed to a method for sterilizing a biological material that is sensitive to radiation and contains a non-aqueous solvent comprising: (i) reducing the residual solvent content of a biological material to a level effective to protect the biological material from radiation; and (ii) irradiating the biological material with radiation at an effective rate for a time effective to sterilize the biological material.

Another preferred embodiment of the present invention is directed to a method for sterilizing a biological material that is sensitive to radiation and contains a non-aqueous solvent comprising: (i) reducing the temperature of a biological material to a level effective to protect the biological material from radiation; and (ii) irradiating the biological material with radiation at an effective rate for a time effective to sterilize the biological material.

Another preferred embodiment of the present invention is directed to a method for sterilizing a biological material that is sensitive to radiation and contains a non-aqueous solvent comprising: (i) applying to the biological material a stabilizing process selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing process and the rate of irradiation are together effective to protect the biological material from radiation.

Another preferred embodiment of the present invention is directed to a method for sterilizing a biological material that is sensitive to radiation and contains a non-aqueous solvent comprising: (i) applying to the biological material at least two stabilizing processes selected from the group consisting of: (a) reducing the residual solvent content of a biological material, (b) adding to the biological material at least one stabilizer, and (c) reducing the temperature of the biological material; and (ii) irradiating the biological material with radiation at an effective rate for a time effective to sterilize the biological material, wherein the stabilizing processes may be performed in any order and are together effective to protect the biological material from radiation.

Another preferred embodiment of the present invention is directed to a composition comprising a biological material and a non-aqueous solvent in an amount effective to preserve the preparation during sterilization with radiation, such that it remains suitable and effective for its intended use.

Another preferred embodiment of the present invention is directed to a composition comprising at least one biological material, a least one non-aqueous solvent and at least one stabilizer, wherein the non-aqueous solvent and stabilizer are together present in an amount effective to preserve the material for its intended use following sterilization with radiation.

The non-aqueous solvent is preferably a non-aqueous solvent that is not prone to the formation of free-radicals upon irradiation, and more preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

According to certain embodiments of the present invention, the biological material may contain a mixture of water and a non-aqueous solvent, such as ethanol and/or acetone. In such embodiments, the non-aqueous solvent(s) is preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

According to certain methods of the present invention, a stabilizer is added prior to irradiation of the biological material which contains a non-aqueous solvent with radiation. This stabilizer is preferably added to the biological material which contains a non-aqueous solvent in an amount that is effective to protect the biological material from the radiation. Alternatively, the stabilizer is added to the biological material which contains a non-aqueous solvent in an amount that, together with the non-aqueous solvent, is effective to protect the biological material from the radiation. Suitable amounts of stabilizer may vary depending upon certain features of the particular method(s) of the present invention being employed, such as the particular stabilizer being used and/or the nature and characteristics of the particular biological material which contains a non-aqueous solvent being irradiated and/or its intended use, and can be determined empirically by one skilled in the art.

According to certain methods of the present invention, the residual solvent content of the biological material which contains a non-aqueous solvent is reduced prior to irradiation of the biological material with radiation. The residual solvent content is preferably reduced to a level that is effective to protect the biological material from the radiation. Suitable levels of residual solvent content may vary depending upon certain features of the particular method(s) of the present invention being employed, such as the nature and characteristics of the particular biological material which contains a non-aqueous solvent being irradiated and/or its intended use, and can be determined empirically by one skilled in the art. There may be biological materials for which it is desirable to maintain the residual solvent content to within a particular range, rather than a specific value.

According to certain embodiments of the present invention, when the biological material which contains a non-aqueous solvent also contains water, the residual solvent (water) content of a biological material may be reduced by dissolving or suspending the biological material which contains a non-aqueous solvent in a non-aqueous solvent that is capable of dissolving water. When the biological material is in liquid phase, the same result may also be achieved by the dilution of the residual solvent (water) by the addition of liquid non-aqueous solvent. Preferably, such a second non-aqueous solvent is not prone to the formation of free-radicals upon irradiation and has little or no dissolved oxygen or other gas(es) that is (are) prone to the formation of free-radicals upon irradiation.

When the biological material which contains a non-aqueous solvent is in a liquid phase, reducing the residual solvent content may be accomplished by any of a number of means, such as by increasing the solute concentration. In this manner, the concentration of protein in the biological material which contains a non-aqueous solvent dissolved within the solvent may be increased to generally at least about 0.5%, typically at least about 1%, usually at least about 5%, preferably at least about 10%, more preferably at least about 15%, even more preferably at least about 20%, still even more preferably at least about 25%, and most preferably at least about 50%.

In certain embodiments of the present invention, the residual solvent content of a particular biological material which contains a non-aqueous solvent may be found to lie within a range, rather than at a specific point. Such a range for the preferred residual solvent content of a particular biological material which contains a non-aqueous solvent may be determined empirically by one skilled in the art.

While not wishing to be bound by any theory of operability, it is believed that the reduction in residual solvent content reduces the degrees of freedom of the biological material which contains a non-aqueous solvent, reduces the number of targets for free radical generation and may restrict the solubility of these free radicals. Similar results might therefore be achieved by lowering the temperature of the biological material which contains a non-aqueous solvent below its eutectic point or below its freezing point, or by vitrification to likewise reduce the degrees of freedom of the biological material. These results may permit the use of a higher rate and/or dose of radiation than might otherwise be acceptable. Thus, the methods described herein may be performed at any temperature that doesn't result in unacceptable damage to the biological material which contains a non-aqueous solvent, i.e., damage that would preclude the safe and effective use of the biological material. Preferably, the methods described herein are performed at ambient temperature or below ambient temperature, such as below the eutectic point or freezing point of the biological material which contains a non-aqueous solvent being irradiated.

The residual solvent content of the biological material which contains a non-aqueous solvent may be reduced by any of the methods and techniques known to those skilled in the art for reducing solvent from a biological material which contains a non-aqueous solvent without producing an unacceptable level of damage to the biological material. Such methods include, but are not limited to, addition of solute, evaporation, concentration, centrifugal concentration, vitrification and spray-drying.

A particularly preferred method for reducing the residual solvent content of a biological material which contains a non-aqueous solvent is lyophilization.

Another particularly preferred method for reducing the residual solvent content of a biological material which contains a non-aqueous solvent is the addition of solute.

Another particularly preferred method for reducing the residual solvent content of a biological material which contains a non-aqueous solvent is spray-drying.

Another particularly preferred method for reducing the residual solvent content of a biological material which contains a non-aqueous solvent is vitrification, which may be accomplished by any of the methods and techniques known to those skilled in the art, including the addition of solute and or additional solutes, such as sucrose, to raise the eutectic point of the biological material which contains a non-aqueous solvent, followed by a gradual application of reduced pressure to the biological material which contains a non-aqueous solvent in order to remove the residual solvent. The resulting glassy material will then have a reduced residual solvent content.

According to certain methods of the present invention, the biological material which contains a non-aqueous solvent to be sterilized may be immobilized upon a solid surface by any means known and available to one skilled in the art. For example, the biological material which contains a non-aqueous solvent to be sterilized may be present as a coating or surface on a biological or non-biological substrate.

The radiation employed, in the methods of the present invention may be any radiation effective for the sterilization of the biological material which contains a non-aqueous solvent being treated. The radiation may be corpuscular, including E-beam radiation. Preferably the radiation is electromagnetic radiation, including x-rays, infrared, visible light, UV light and mixtures of various wavelengths of electromagnetic radiation. A particularly preferred form of radiation is gamma radiation.

According to the methods of the present invention, the biological material which contains a non-aqueous solvent is irradiated with the radiation at a rate effective for the sterilization of the biological material, while not producing an unacceptable level of damage to that material. Suitable rates of irradiation may vary depending upon certain features of the methods of the present invention being employed, such as the nature and characteristics of the particular biological material, which may contain a non-aqueous solvent, being irradiated, the particular form of radiation involved and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low ($\leq 3$ kGy/hour) and high ($>3$ kGy/hour) rates may be utilized in the methods described herein to achieve such results. The rate of irradiation is preferably selected to optimize the recovery of the biological material which contains a non-aqueous solvent while still sterilizing the biological material which contains a non-aqueous solvent. Although reducing the rate of irradiation may serve to decrease damage to the biological material which contains a non-aqueous solvent, it will also result in longer irradiation times being required to achieve a particular desired total dose. A higher dose rate may therefore be preferred in certain circumstances, such as to minimize logistical issues and costs, and may be possible when used in accordance with the methods described herein for protecting a biological material which contains a non-aqueous solvent from irradiation.

According to a particularly preferred embodiment of the present invention, the rate of irradiation is not more than about 3.0 kGy/hour, more preferably between about 0.1 kGy/hr and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr, more preferably at least about 6 kGy/hr, even more preferably at least about 16 kGy/hr, and even more preferably at least about 30 kGy/hr and most preferably at least about 45 kGy/hr or greater.

According to the methods of the present invention, the biological material which contains a non-aqueous solvent to be sterilized is irradiated with the radiation for a time effective for the sterilization of the biological material. Combined with irradiation rate, the appropriate irradiation time results in the appropriate dose of irradiation being applied to the biological material which contains a non-aqueous solvent. Suitable irradiation times may vary depending upon the particular form and rate of radiation involved and/or the nature and characteristics of the particular biological material which contains a non-aqueous solvent being irradiated. Suitable irradiation times can be determined empirically by one skilled in the art.

According to the methods of the present invention, the biological material which contains a non-aqueous solvent to be sterilized is irradiated with radiation up to a total dose effective for the sterilization of the biological material, while not producing an unacceptable level of damage to that material. Suitable total doses of radiation may vary depending upon certain features of the methods of the present invention being employed, such as the nature and characteristics of the particular biological material which contains a non-aqueous solvent being irradiated, the particular form of radiation involved and/or the particular biological contaminants or pathogens being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy or greater.

The particular geometry of the biological material which contains a non-aqueous solvent being irradiated, such as the thickness and distance from the source of radiation, may be determined empirically by one skilled in the art. A preferred embodiment is a geometry that provides for an even rate of irradiation throughout the preparation. A particularly preferred embodiment is a geometry that results in a short path length for the radiation through the preparation, thus minimizing the differences in radiation dose between the front and back of the preparation. This may be further minimized in some preferred geometries, particularly those wherein the preparation has a constant radius about its axis that is perpendicular to the radiation source, by the utilization of a means of rotating the preparation about said axis.

Similarly, according to certain methods of the present invention, an effective package for containing the preparation during irradiation is one which combines stability under the influence of irradiation, and which minimizes the interactions between the package and the radiation. Preferred packages maintain a seal against the external environment before, during and post-irradiation, and are not reactive with the preparation within, nor do they produce chemicals that may interact with the preparation within. Particularly preferred examples include but are not limited to containers that comprise glasses stable when irradiated, stoppered with stoppers made of rubber that is relatively stable during radiation and liberates a minimal amount of compounds from within, and sealed with metal crimp seals of aluminum or other suitable materials with relatively low Z numbers. Suitable materials can be determined by measuring their physical performance, and the amount and type of reactive leachable compounds post-irradiation and by examining other characteristics known to be important to the containment of biological materials empirically by one skilled in the art.

According to certain methods of the present invention, an effective amount of at least one sensitizing compound may optionally be added to the biological material which contains a non-aqueous solvent prior to irradiation, for example to enhance the effect of the irradiation on the biological contaminant(s) or pathogen(s) therein, while employing the methods described herein to minimize the deleterious effects of irradiation upon the biological material. Suitable sensitizers are known to those skilled in the art, and include psoralens and their derivatives and inactines and their derivatives.

According to the methods of the present invention, the irradiation of the biological material which contains a non-aqueous solvent may occur at any temperature that is not deleterious to the biological material being sterilized. According to one preferred embodiment, the biological material which contains a non-aqueous solvent is irradiated at ambient temperature. According to an alternate preferred embodiment, the biological material which contains a non-aqueous solvent is irradiated at reduced temperature, i.e., a temperature below ambient temperature, such as $0°$ C., $-20°$ C., $-40°$ C., $-60°$ C., $-78°$ C. or $-196°$ C. According to this embodiment of the present invention, the biological material which contains a non-aqueous solvent is preferably irradiated at or below the freezing or eutectic point of the biological material. According to another alternate preferred embodiment, the biological material which contains a non-aqueous solvent is irradiated at elevated temperature, i.e., a temperature above ambient temperature, such as $37°$ C., $60°$ C., $72°$ C. or $80°$ C. While not wishing to be bound by any theory, the use of elevated temperature may enhance the effect of irradiation on the biological contaminant(s) or pathogen(s) and therefore allow the use of a lower total dose of radiation.

Most preferably, the irradiation of the biological material which contains a non-aqueous solvent occurs at a temperature that protects the preparation from radiation. Suitable temperatures can be determined empirically by one skilled in the art.

In certain embodiments of the present invention, the temperature at which irradiation is performed may be found to lie within a range, rather than at a specific point. Such a range for the preferred temperature for the irradiation of a particular biological material which contains a non-aqueous solvent may be determined empirically by one skilled in the art.

According to the methods of the present invention, the irradiation of the biological material which contains a non-aqueous solvent may occur at any pressure which is not deleterious to the biological material which contains a non-aqueous solvent being sterilized. According to one preferred embodiment, the biological material which contains a non-aqueous solvent is irradiated at elevated pressure. More preferably, the biological material which contains a non-aqueous solvent is irradiated at elevated pressure due to the application of sound waves or the use of a volatile. While not wishing to be bound by any theory, the use of elevated pressure may enhance the effect of irradiation on the biological contaminant(s) or pathogen(s) and/or enhance the protection afforded by one or more stabilizers, and therefore allow the use of a lower total dose of radiation. Suitable pressures can be determined empirically by one skilled in the art.

Generally, according to the methods of the present invention, the pH of the biological material which contains a non-aqueous solvent undergoing sterilization is about 7. In some embodiments of the present invention, however, the biological material which contains a non-aqueous solvent may have a pH of less than 7, preferably less than or equal to 6, more preferably less than or equal to 5, even more preferably less than or equal to 4, and most preferably less than or equal to 3. In alternative embodiments of the present invention, the biological material which contains a non-aqueous solvent may have a pH of greater than 7, preferably greater than or equal to 8, more preferably greater than or equal to 9, even more preferably greater than or equal to 10, and most preferably greater than or equal to 11. According to certain embodiments of the present invention, the pH of the preparation undergoing sterilization is at or near the isoelectric point of one of the components of the biological material. Suitable pH levels can be determined empirically by one skilled in the art.

Similarly, according to the methods of the present invention, the irradiation of the biological material which contains a non-aqueous solvent may occur under any atmosphere that is not deleterious to the biological material being treated. According to one preferred embodiment, the biological material which contains a non-aqueous solvent is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the biological material which contains a non-aqueous solvent is held under vacuum while being irradiated. According to a particularly preferred embodiment of the present invention, a biological material which contains a non-aqueous solvent (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment of the present invention, a liquid biological material which contains a non-aqueous solvent is held under low pressure, to decrease the amount of gas, particularly oxygen, dissolved in the liquid, prior to irradiation, either with or without a prior step of solvent reduction, such as lyophilization. Such degassing may be performed using any of the methods known to one skilled in the art.

In another preferred embodiment, where the biological material which contains a non-aqueous solvent contains oxygen or other gases dissolved within or associated with it, the amount of these gases within or associated with the preparation may be reduced by any of the methods and techniques known and available to those skilled in the art, such as the controlled reduction of pressure within a container (rigid or flexible) holding the preparation to be treated or by placing the preparation in a container of approximately equal volume.

In certain embodiments, when the biological material which contains a non-aqueous solvent to be treated is a tissue, at least one stabilizer is introduced according to any of the methods and techniques known and available to one skilled in the art, including soaking the tissue in a solution containing the stabilizer(s), preferably under pressure, at elevated temperature and/or in the presence of a penetration enhancer, such as dimethylsulfoxide. Other methods of introducing at least one stabilizer into a tissue include, but are not limited to, applying a gas containing the stabilizer(s), preferably under pressure and/or at elevated temperature, injection of the stabilizer(s) or a solution containing the stabilizer(s) directly into the tissue, placing the tissue under reduced pressure and then introducing a gas or solution containing the stabilizer(s) and combinations of two or more of these methods. One or more sensitizers may also be introduced into a tissue according to such methods.

It will be appreciated that the combination of one or more of the features described herein may be employed to further minimize undesirable effects upon the biological material which contains a non-aqueous solvent caused by irradiation, while maintaining adequate effectiveness of the irradiation process on the biological contaminant(s) or pathogen(s). For example, in addition to the use of a stabilizer, a particular biological material which contains a non-aqueous solvent may also be lyophilized, held at a reduced temperature and kept under vacuum prior to irradiation to further minimize undesirable effects.

The sensitivity of a particular biological contaminant or pathogen to radiation is commonly calculated by determining the dose necessary to inactivate or kill all but 37% of the agent in a sample, which is known as the $D_{37}$ value. The desirable components of a biological material may also be considered to have a $D_{37}$ value equal to the dose of radiation required to eliminate all but 37% of their desirable biological and physiological characteristics.

In accordance with certain preferred methods of the present invention, the sterilization of a biological material which contains a non-aqueous solvent is conducted under conditions that result in a decrease in the $D_{37}$ value of the biological contaminant or pathogen without a concomitant decrease in the $D_{37}$ value of the biological material. In accordance with other preferred methods of the present invention, the sterilization of a biological material which contains a non-aqueous solvent is conducted under conditions that result in an increase in the $D_{37}$ value of the material. In accordance with the most preferred methods of the present invention, the sterilization of a biological material which contains a non-aqueous solvent is conducted under conditions that result in a decrease in the $D_{37}$ value of the biological contaminant or pathogen and a concomitant increase in the $D_{37}$ value of the biological material.

EXAMPLES

The following examples are illustrative, but not limiting, of the present invention. Other suitable modifications and adaptations are of the variety normally encountered by those skilled in the art and are fully within the spirit and scope of the present invention. Unless otherwise noted, all irradiation was accomplished using a $^{60}$Co source.

Example 1

In this experiment, the effect of gamma radiation on dried urokinase suspended in polypropylene glycol (PPG) 400 or phosphate buffered saline (PBS) was determined.

Method

Six 1.5 ml polypropylene microfuge tubes containing urokinase and PPG400 (tubes 2 and 5), PBS (tubes 3 and 6) or dry urokinase alone (tubes 1 and 4) were prepared as indicated in the table below. Tubes 4-6 were gamma irradiated at 45 kGy (1.9 kGy/hr) at 4° C. Tubes 1-3 were controls (4° C.).

| Tube | Sample | weight of dry urokinase (mg) | volume PPG400 (ul) | volume PBS (ul) |
|---|---|---|---|---|
| 1 | dry urokinase alone | 3.2 | 0 | 0 |
| 2 | urokinase suspended in PPG400 | 3.16 | 126 | 0 |
| 3 | urokinase suspended in PBS | 3.08 | 0 | 123 |
| 4 | dry urokinase alone | 3.38 | 0 | 0 |
| 5 | urokinase suspended in PPG400 | 3.3 | 132 | 0 |
| 6 | urokinase suspended in PBS | 3.52 | 0 | 141 |

After irradiation, the samples were centrifuged at room temperature for 5 minutes at 14 k RPM. PPG400 solvent was removed from tubes 2 and 5 and 120 µl PBS were added to those two tubes. 128 µl and 135 µl PBS were added to tubes 1 and 4, respectively (urokinase concentration of 40,000 IU/ml). All samples were then diluted 50-fold with PBS and absorbance at 280 nm was determined. 50 µl of each diluted sample were then added to a 96-well microtiter plate, followed by 50 µl of 3 mM substrate in 2× assay buffer. The plates were incubated at 37° C. with shaking and absorption read at both 405 and 620 nm every 20 minutes beginning 5 minutes after substrate addition. The absorption at 630 nm (background) was subtracted from the value at 405 nm to obtain a corrected absorption value. The final concentration of urokinase was 1000 IU/ml.

Materials

Urokinase—Sigma cat. # U-5004, lot 29H1054; 2.5 mg=4000 IU Urokinase.

PPG400—Fluka cat. # 81350.

Substrate—urokinase substrate 1, colormetric—Calbiochem. cat. # 672157, lot B23901, 5 mg vials, final concentration 1.5 mM.

2× Assay Buffer—100 mM Tris (pH 8.8), 100 mM NaCl, 0.2% PEG8000.

Results

Urokinase suspended in PPG400 and then gamma irradiated to a total dose of 45 kGy maintained the same percent activity as gamma irradiated dry powder urokinase (80%). In contrast, urokinase suspended in PBS subjected to the same gamma irradiation maintained only 6% activity. The results of this experiment are presented in FIG. 1.

Example 2

In this experiment, the activity (as shown by the ability to bind antigen) of immobilized anti-insulin monoclonal antibody was determined after irradiation in the presence of various forms of polypropylene glycol (molecular weights of 400, 1200 and 2000).

Method

In two 96-well microliter plates (falcon plates—ProBind polystyrene cat. # 353915), the wells were washed four times with full volume PBS (pH 7.4). Once the two plates were prepared as described above, they were coated with 100 µl/well of freshly prepared 2 µg/ml anti-insulin in coating buffer and left overnight at 4° C. The plates were then washed briefly three times with PBS (pH 7.4) and 100 µl of PPG400, PPG1200 or PPG2000 were added to specific wells. Each solution was prepared in a 11, i.e., 2-fold, dilution series with PBS. Both plates were covered tightly with a cap mat (Greiner cap mat cat. # 381070 (USA Scientific)) and irradiated at either 0 kGy/hr or 45 kGy (1.92 kGy/hr), both at 4° C.

Following irradiation, approximately 380 µl full volume blocking buffer were added to all wells and the plates were incubated for two hours at 37° C. The plates were washed four times with TBST and 100 µl of 50 ng/ml biotin-labelled insulin in binding buffer were added to each well. The plates were covered with a plate sealer (Dynatech acetate plate sealers) and incubated at 37° C. with shaking (LabLine Titer Plate Shaker set at 3) for 1.5 hours. The plates were washed four times with TBST and 100 µl of 0.5 µg/ml phosphatase-labelled streptavidin in binding buffer were added to each well. The plates were covered with a plate sealer and incubated at 37° C. for one hour with shaking. The plates were then washed four times with TBST and 100 µl of 1 mg/ml phosphatase substrate in DEA buffer were added to each well and the plates were incubated at 37° C. with shaking. Absorption was read at both 405 and 620 nm at 5 minute intervals as needed. The absorption at 630 nm (background) was subtracted from the value at 405 nm to obtain a corrected absorption value.

Materials

Blocking buffer—2% BSA/PBS (pH 7.4).

TBST—Tris Buffered Saline (pH 7.4) with 0.05% Tween 20.

Biotin-Labelled Insulin—from bovine pancreas—Sigma 1-2258 lot 110H8065, 5 mg insulin, 1.2 mol. FITC per mol, insulin, reconstituted in 5 ml sterile water at 1.0 mg/ml stored at 4° C.

Binding Buffer—0.25% BSA/PBS (pH 7.4).

Phosphatase-Labelled Streptavidin—KPL cat. # 15-30-00; 05 mg/ml in 50% glycerol/$H_2O$ (stock diluted 1:1000).

DEA Buffer—per 1 L-97 ml diethanolamine (Sigma D-8885), 0.1 g $MgCl_2.6H_2O$, 0.02% sodium azide, stored at 4° C.

Phosphatase Substrate—p-nitrophenyl phosphate—Sigma 104-105, 5 mg/tablet. The phosphatase substrate was prepared fresh as a 1 mg/ml solution in phosphatase substrate buffer, i.e., DEA buffer. The solution is light sensitive so it had to be stored in the dark until ready to dispense.

Monoclonal IgG1 anti-Human Insulin—Biodesign Int. cat. # E86102M, lot 8J2877.

Coating Buffer—carbonate/bicarbonate (pH 9.4).

Polypropylene glycol P400—Fluka cat. # 81350.

Polypropylene glycol P1200—Fluka cat. # 81370.

Polypropylene glycol P2000—Fluka cat. # 81380.

Results

Figure 2:
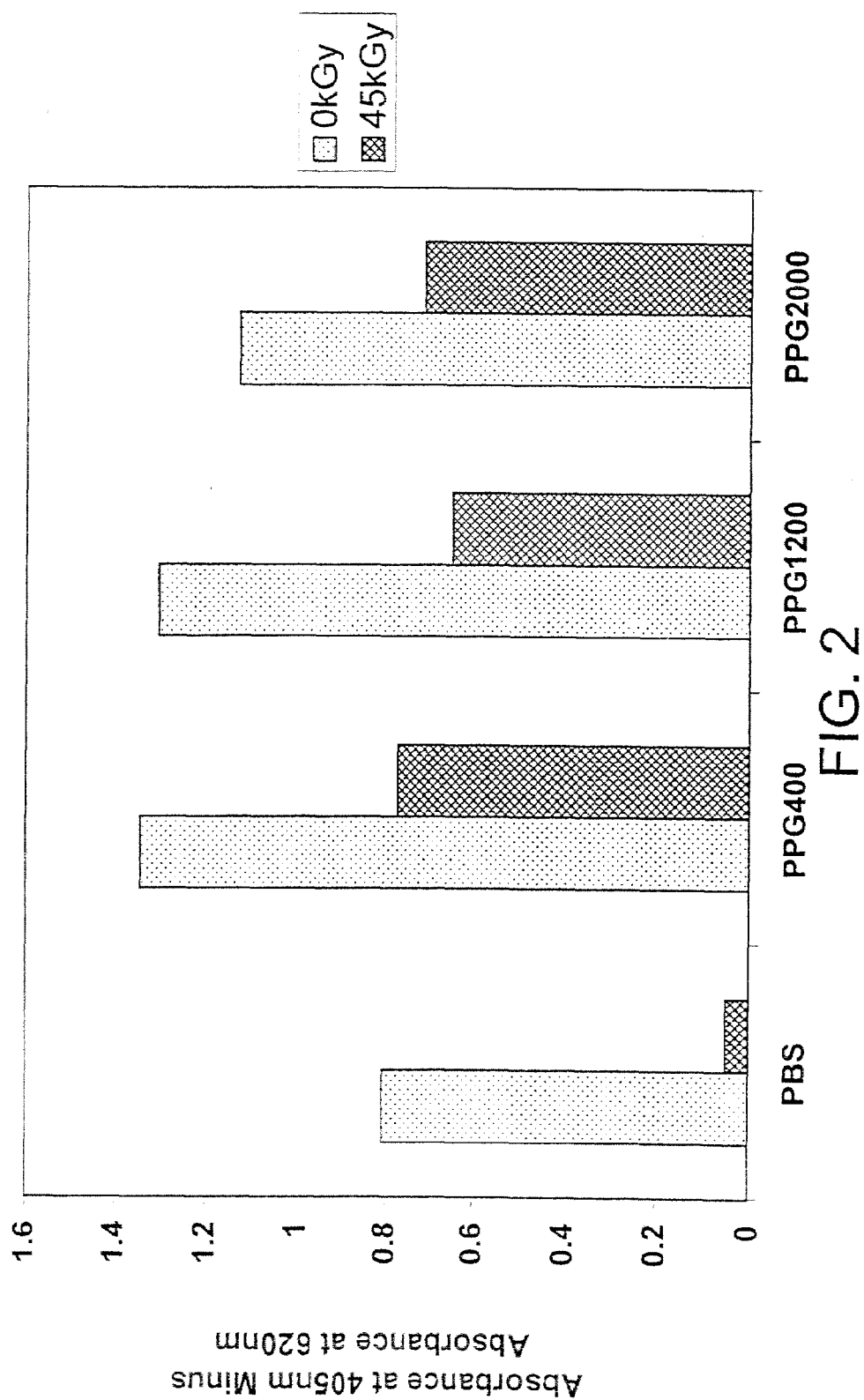
FIG. 2 is a graph showing the activity of immobilized anti-insulin monoclonal antibody after irradiation in the presence of various forms of polypropylene glycol.

Irradiated samples containing PPG exhibited approximately 50-63% of binding activity of unirradiated control. In contrast, irradiated samples containing PBS exhibited no binding activity. The results are presented in FIG. 2.

Example 3

In this experiment, liquid thrombin containing 50% glycerol and spiked with porcine parvovirus (PPV) was irradiated to varying total doses of radiation.

Method

1. Add 100 µl 100% glycerol, 20 µl thrombin (100 U/ml thrombin) spiked with 50 µl PPV and optionally 20 µl (200 mM) sodium ascorbate as a stabilizer (adjusted to a total volume of 1 ml with $H_2O$) to Wheaton 3 ml tubes (in duplicate), and irradiate to a total dose of 10, 30 or 45 kGy at 1.8 kGy/hr at 4° C.

2. Label and seed 96-well cell culture plates to allow at least 4 well per dilution (seeding to be done one day before inoculation). Add 200 μl of cell suspension per well at a concentration of 4×10⁴/ml. The same cell culture medium is used for cell growth and maintenance after virus inoculation.
3. Perform virus inoculation when the cells sheets are 70-90% confluent. In this experiment 800 μl PK-13 growth media was added to 200 μl samples first.
4. Make appropriate dilution (1:5) of samples with PK-13 growth media, then filter sterilize each sample using low-protein-binding disc filters.
5. Add 50 μl of the pre-diluted sample to column 1 of a 96-well plate. In column 1 mix the medium and the sample together by pipetting up and down 4-5 times. With fresh tips transfer the necessary amount (50 μl) to the next column and repeat the mixing process. Empty all the liquid out of the tips and using the same set of tips, transfer the sample to the next column. Repeat this process in each column until column 12 is reached. When the sample in column 12 is mixed, empty the liquid out of the tips, withdraw the sample amount and dispose of this extra liquid in a waste bottle. This gives you 12 samples dilutions.
6. Return plates to the incubator at 37° C.
7. Observe microscopically and record the cytopathic effect in inoculated cultures on day 4-5 and day 7. The $TCID_{50}$ is calculated from CPE reading according to the method of Kärber.
8. Positive controls were done by adding 50 μl PPV infecting stock, and negative controls were done by adding 50 μl PK-13 growth media followed by serial 1:5 dilutions.

Materials

Wheaton tubes—glass serum vials, Wheaton # 223684, lot # 1154132-02.

Thrombin—bovine origin, 5000 US Units (5000 U/ml stock).

Sodium Ascorbate—Aldrich Chem. Co. cat. # 26,855-0 (Milw, Wis. 53201).

Porcine Parvovirus (PPV)—ATCC # VR-742; PPV infecting stock was prepared by PEG8000 preparation wherein ⅕ volume of PEG8000 (20% in 2.5 M NaCl) was added to PPV and incubated at refrigerated temperatures for 24 hours after which, PPV was pelleted by 15,000 rpm for 45 minutes in a Beckman SW-28 rotor, and resuspended in ¹⁄₁₀ volume of PEG buffer. PPV titer of porcine parvovirus was determined by $TCID_{50}$ and was about 9.0 log/ml (032301 stock). PPV spike ratio was 1:4 (50 μl PPV stock mixed with 150 μl protein solution) into liquid thrombin.

PEG Buffer—0.1 M NaCl, 0.01 M Tris (pH 7.4), 1 mM EDTA.

Siliconized stoppers were used in the experiment obtained from American Stemli (Princeton, N.J.), 6720GC rubber formulation, lot # G009/7202.

Cells—PK-13 (ATCC # CRL-6489), passage # 14. Cells are maintained in PK-13 growth medium (Dulbecco's modified Eagle medium supplemented with 10% FBS and 1× pencillin/streptomycin/L-glutamine).

Results

| Sample | $TCID_{50}$ Titer per 0.05 ml | Log Reduction |
|---|---|---|
| 0 kGy/+200 mM sodium ascorbate | 6.29 | |
| 0 kGy/no stabilier | 6.375 | |
| 10 kGy/+200 mM sodium ascorbate | 4.97 | 1.32 |

-continued

| Sample | $TCID_{50}$ Titer per 0.05 ml | Log Reduction |
|---|---|---|
| 10 kGy/no stabilizer | 2.97 | 3.405 |
| 30 kGy/+200 mM sodium ascorbate | 3.05 | 3.24 |
| 30 kGy/no stabilizer | 2.35 | 4.025 |
| 45 kGy/+200 mM sodium ascorbate | 3.05 | 3.24 |
| 45 kGy/no stabilizer | 3.05 | 3.325 |

With a 10 kGy total dose, there was a 1.32 log and a 3.405 log reduction in PPV levels in the presence and absence of sodium ascorbate, respectively. Similarly, with a 30 kGy total dose, there was a 3.24 log and a 4.025 log reduction in PPV levels in the presence or absence, respectively, of sodium ascorbate. With a 45 kGy total dose, there was a 3.24 log and a 3.325 log reduction in PPV levels with or without ascorbate, respectively. This experiment demonstrates that inactivation of even small non-enveloped viruses is effective in the presence of a non-aqueous solvent both with and without an effective stabilizer.

Example 4

In this experiment, trypsin suspended in polypropylene glycol 400 was subjected to gamma irradiation at varying levels of residual solvent (water) content.

Method

Trypsin was suspended in polypropylene glycol 400 at a concentration of about 20,000 U/ml and divided into multiple samples. A fixed amount of water (0%, 1%, 2.4%, 4.8%, 7%, 9%, 10%, 20%, 33%) was added to each sample; a 100% water sample was also prepared which contained no PPG 400.

Samples were irradiated to a total dose of 45 kGy at a rate of 1.9 kGy/hr and a temperature of 4° C. Following irradiation, each sample was centrifuged to pellet the undissolved trypsin. The PPG/water soluble fraction was removed and the pellets resuspended in water alone for activity testing.

Assay conditions: 5 U/well trypsin (50 U/ml)+BAPNA substrate (0.5 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

Figure 3:
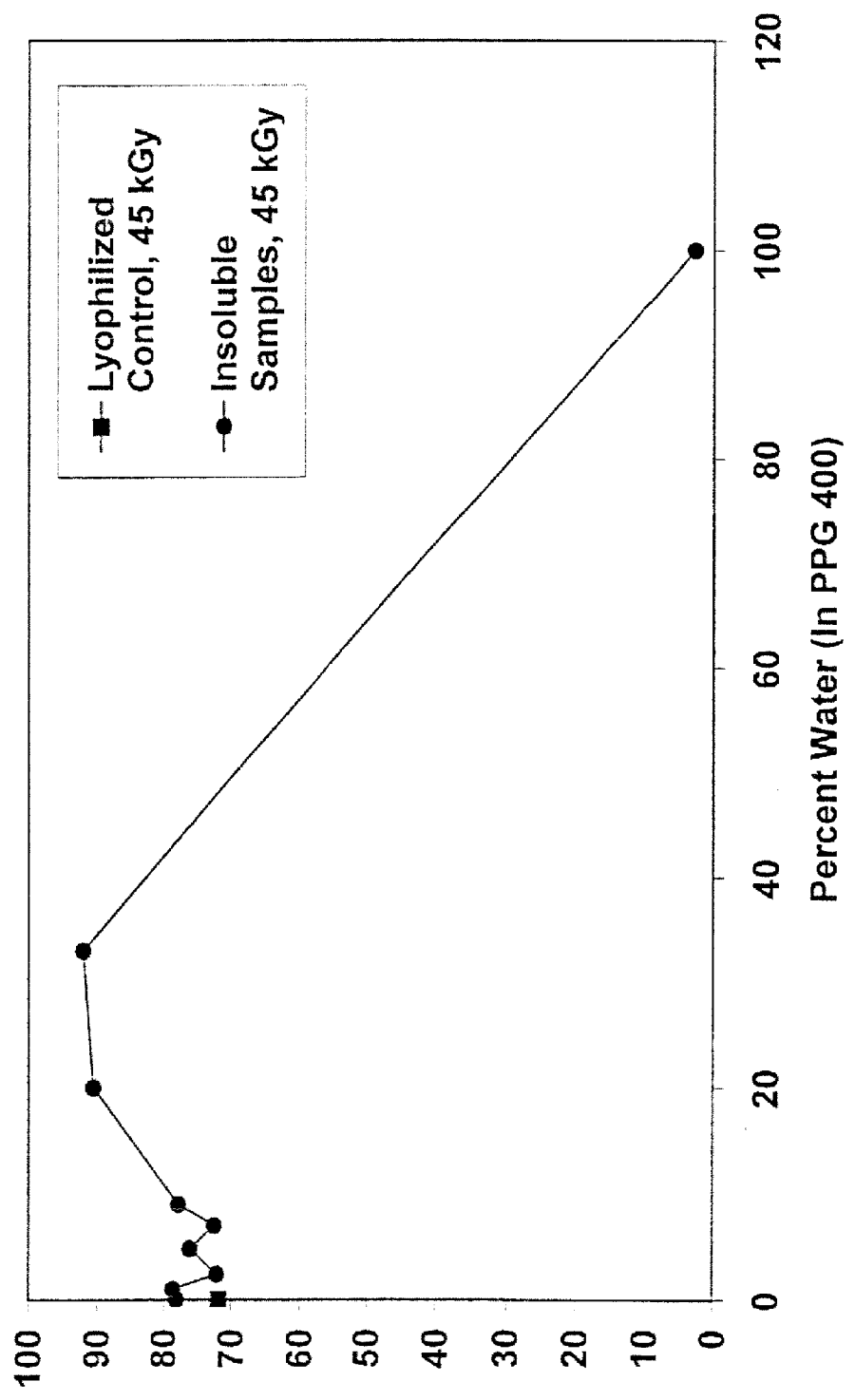
FIG. 3 is a graph showing the effect of gamma radiation on trypsin suspended in polypropylene glycol at varying levels of residual solvent (water) content.

The irradiated samples containing a mixture of polypropylene glycol (PPG 400) and water (up to 33% water) retained about 80% of the activity of an unirradiated trypsin control and activity equal to that of a dry (lyophilized) trypsin control irradiated under identical conditions. No activity was detected in the 100% water sample irradiated to 45 kGy. The results of this experiment are shown graphically in FIG. 3.

Example 5

In this experiment, porcine heart valves were gamma irradiated in the presence of polypropylene glycol 400 (PPG400) and, optionally, a scavenger, to a total dose of 30 kGy (1.584 kGy/hr at −20° C.).

Materials:

Tissue—Porcine Pulmonary Valve (PV) Heart valves were harvested prior to use and stored.

Tissue Preparation Reagents—
 Polypropylene Glycol 400. Fluka, cat# 81350 lot# 386716/1
 Trolox C. Aldrich, cat# 23,881-3 lot#02507TS
 Coumaric Acid. Sigma, cat# C-9008 lot# 49H3600
 n-Propyl Gallate. Sigma, cat# P-3130 lot# 117H0526
 α-Lipoic Acid. CalBiochem, cat# 437692 lot#B34484
 Dulbecco's PBS. Gibco BRL cat# 14190-144 lot# 1095027
 2.0 ml Screw Cap tubes. VWR Scientific Products, cat# 20170-221 lot# 0359

Tissue Hydrolysis Reagents—
 Nerl $H_2O$, NERL Diagnostics cat# 9800-5 lot# 03055151
 Acetone. EM Science cat# AX0125-5, lot# 37059711
 6 N constant boiling HCl. Pierce cat# 24309, lot# BA42184
 Int-Pyd (Acetylated Pyridinoline) HPLC Internal Standard. Metra Biosystems Inc. cat# 8006, lot# 9
 Hydrochloric Acid. VWR Scientific cat# VW3110-3, lot# n/a
 Heptafluorobutyric Acid (HFBA) Sigma cat# H-7133, lot# 20K3482
  FW 214.0 store at 2-8° C.
 SP-Sephadex C-25 resin. Pharmacia cat# 17-0230-01, lot# 247249 (was charged with NaCl as per manufacturer suggestion)

Hydrolysis vials—10 mm×100 mm vacuum hydrolysis tubes. Pierce cat# 29560, lot #BB627281

Heating module—Pierce, Reacti-therm. Model# 18870, S/N 1125000320176

Savant—Savant Speed Vac System:
 1. Speed Vac Model SC110, model # SC110-120, serial # SC110-SD171002-1H
  a. Refrigerated Vapor Trap Model RVT100, model # RVT100-120V, serial # RVT100-58010538-1B
  b. Vacuum pump, VP 100 Two Stage Pump Model VP100, serial # 93024

Column—Phenomenex, Luna 5μ C18(2) 100 Å, 4.6×250 mm. Part # 00G-4252-E0, S/N#68740-25, B/N# 5291-29

HPLC System: Shimadzu System Controller SCL-10A
 Shimadzu Automatic Sample Injector SIL-10A (50 μl loop)
 Shimadzu Spectrofluorometric Detector RF-10A
 Shimadzu Pumps LC-10AD
 Software—Class-VP version 4.1

Low-binding tubes—MiniSorp 100×15 Nunc-Immunotube. Batch # 042950, cat# 468608

Methods:

A. Preparation of Stabilizer Solutions:

Trolox C:
 MW=250; therefore, want 250 mg/ml for 1M or 125 mg/ml for 0.5 M
 actual weight=250.9 mg
 250÷125 mg/ml=2.0 ml Not soluble; therefore an additional 2 ml of PPG was added. After water bath sonication and time, Trolox C is soluble at 125 mM.

Coumaric Acid:
 MW=164; therefore, 164 mg/ml for 1 M
 actual weight=164.8 mg
 164.8 mg÷164 mg/ml=1.0 ml Water bath sonicated for approximately 15 minutes—not 100% soluble. An additional 1 ml PPG was added and further water bath sonicated.

n-Propyl Gallate:
 MW=212.2; therefore, 212 mg/ml for 1M or 106 mg/ml for 0.5 M
 actual weight=211.9 mg
 211.9 mg÷106 mg/ml=2.0 ml Soluble after a 20-30 minute water bath sonication.

1 M α-Lipoic Acid:
 MW=206; therefore, 206 mg/ml
 actual weight=412 mg
 412 mg÷206 mg/ml=2.0 ml Very soluble after 10 minute water bath sonication.
 Final Stocks of Scavengers:
 125 mM Trolox C—4 ml
 1 M Lipoic Acid—2 ml
 0.5 M Coumaric acid—2 ml
 0.5 M n-Propyl Gallate—2 ml B. Treatment of Valves Prior to Gamma-Irradiation.
 1. PV heart valves were thawed on wet ice.
 2. Cusps were dissected out from each valve and pooled into 50 ml conical tubes containing cold Dulbecco's PBS.
 3. Cusps were washed in PBS at 4° C. for approximately 1.5 hrs; changing PBS during that time a total of 6×.
 4. 2 cusps were placed in each 2 ml screw cap tubes.
 5. 1.2 ml of the following were added to two tubes (for 0 and 30 kGy):
 PPG
 125 mM Trolox C in PPG SCb stabilizer mixture—comprising of 1.5 ml 125 mM Trolox C, 300 μl 1 M Lipoic Acid, 600 μl 0.5 M Coumaric Acid and 600 μl 0.5 M n-Propyl Gallate. (Final concentrations: 62.5 mM, 100 mM, 100 mM and 100 mM respectively.)
 6. Tubes were incubated at 4° C., with rocking.
 7. Stabilizer solutions and cusps were transferred into 2 ml glass vials for gamma-irradiation.
 8. All vials were frozen on dry ice.
 9. Control samples were kept in-house at −20° C.

C. Gamma-Irradiation of Tissue.
 Samples were irradiated at a rate of 1.584 kGy/hr at −20° C. to a total dose of 30 kGy.

D. Processing Tissue for Hydrolysis/Extraction.
 1. Since PPG is viscous, PBS was added to allow for easier transfer of material.
 2. Each pair of cusps (2 per condition) were placed into a 50 ml Falcon tube filled with cold PBS and incubated on ice-inverting tubes periodically.
 3. After one hour PBS was decanted from the tubes containing cusps in PPG/0 and 30 and replenished with fresh cold PBS. For the PPG samples containing Trolox C or stabilizer cocktail, fresh 50 ml Falcon tubes filled with cold PBS were set-up and the cusps transferred.
 4. An additional 3 washes were done.
 5. One cusp was transferred into a 2 ml Eppendorf tube filled with cold PBS for extraction. The other cusp was set-up for hydrolysis.

E. Hydrolysis of Tissue.

Hydrolysis of tissue:
1. Each cusp was washed 6× with acetone in an Eppendorf tube (approximately 1.5 ml/wash).
2. Each cusp was subjected to SpeedVac (with no heat) for approximately 15 minutes or until dry.
3. Samples were weighed, transferred to hydrolysis vials and 6 N HCl added at a volume of 20 mg tissue/ml HCl:

| Sample ID | Dry Weight (mg) | µl 6 N HCl |
|---|---|---|
| 1. PPG/0 | 6.49 | 325 |
| 2. PPG/30 | 7.26 | 363 |
| 3. PPG T/0 | 5.80 | 290 |
| 4. PPG T/30 | 8.20 | 410 |
| 5. PPG SCb/0 | 6.41 | 321 |
| 6. PPG SCb/30 | 8.60 | 430 |

4. Samples were hydrolyzed at 110° C. for approximately 23 hours.
5. Hydrolysates were transferred into Eppendorf tubes and centrifuged @ 12,000 rpm for 5 min.
6. Supernatent was then transferred into a clean Eppendorf.
7. 50 µl of hydrolysate was diluted in 8 ml Nerl $H_2O$ (diluting HCl to approximately 38 mM).
8. Spiked in 200 µl of 2×int-pyd. Mixed by inversion. (For 1600 µl 2×int-pyd:160 µl 20×int-pyd+1440 µl Nerl $H_2O$.)
9. Samples were loaded onto SP-Sephadex C25 column (approximately 1×1 cm packed bed volume) that had been equilibrated in water. (Column was pre-charged with NaCl)
10. Loaded flow through once again over column.
11. Washed with 20 ml 150 mM HQ.
12. Eluted crosslinks with 5 ml 2 N HCl into a low binding tube.
13. Dried entire sample in Savant.

F. Analysis of Hydrolysates.

Set-up the following:

| Sample | µl | µl $H_2O$ | µl HFBA |
|---|---|---|---|
| 1. PPG/0 kGy | 18 | 180 | 2 |
| 2. PPG/30 kGy | 59 | 139 | 2 |
| 3. PPG T/0 kGy | 67 | 171 | 2 |
| 4. PPG T/30 kGy | 64 | 134 | 2 |
| 5. PPG SCb/0 kGy | 10 | 188 | 2 |
| 6. PPG SCb/30 kGy | 32 | 166 | 2 |

Figure 4A:
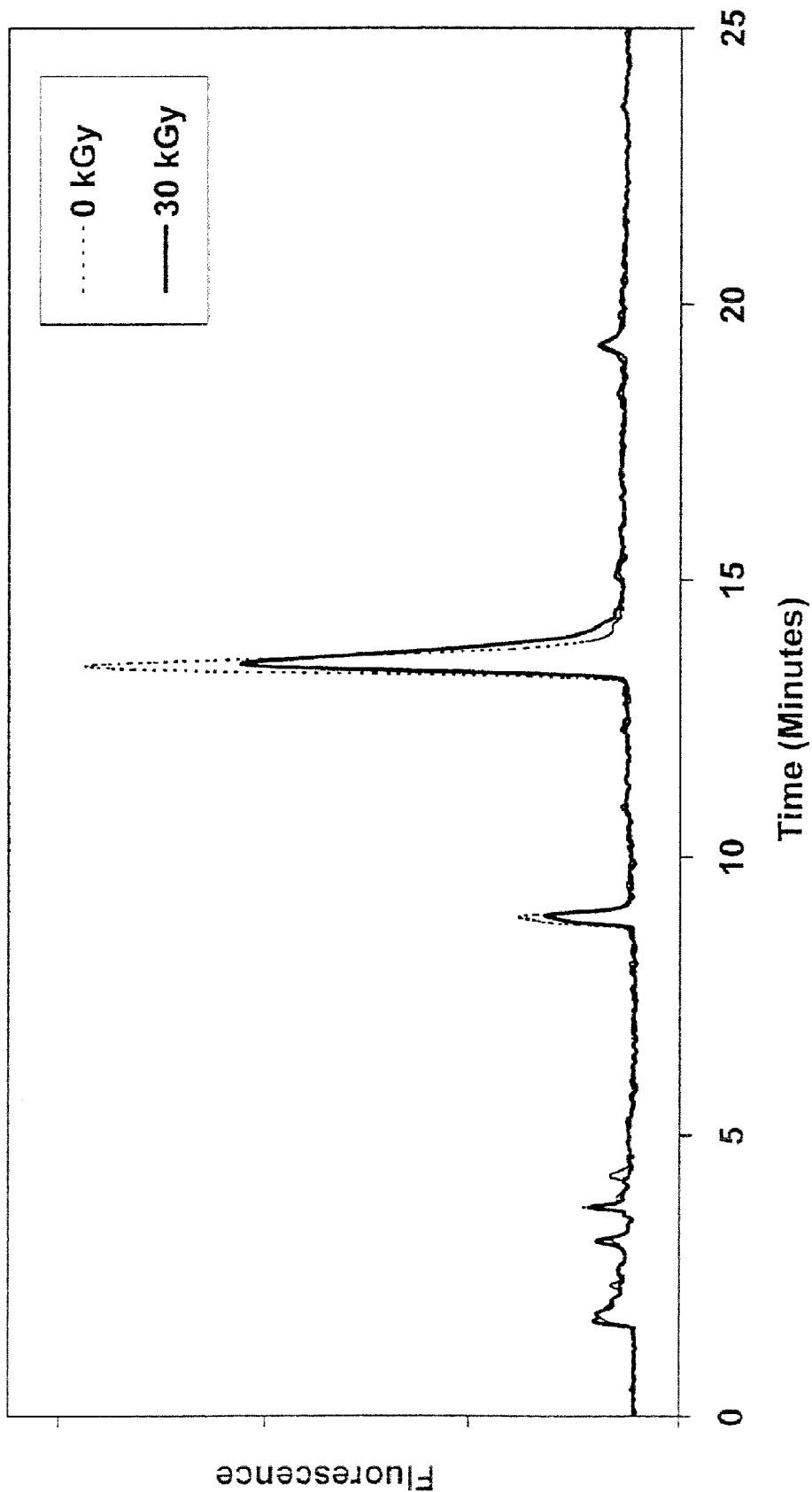
Figure 4C:
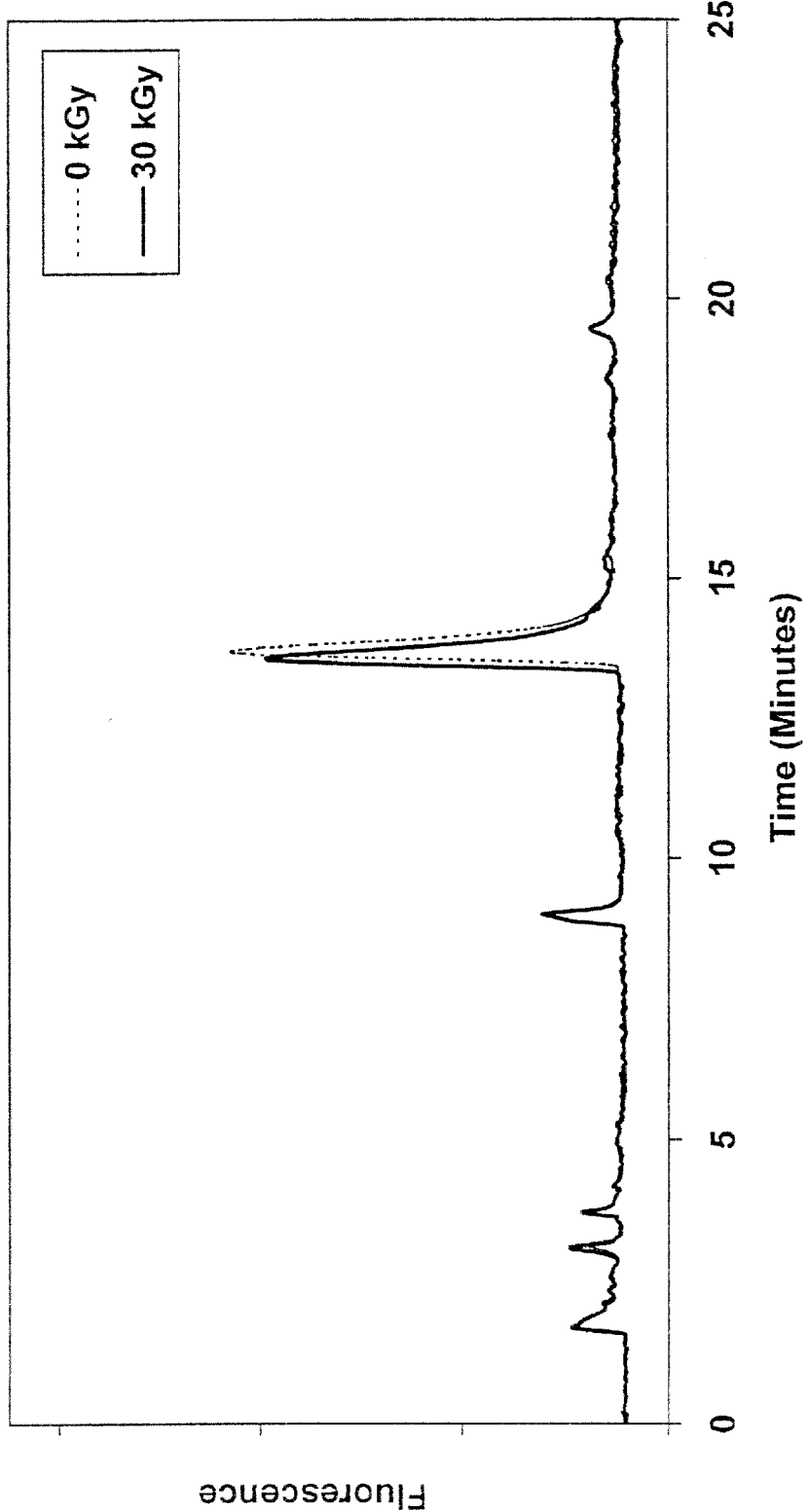
Figure 4D:
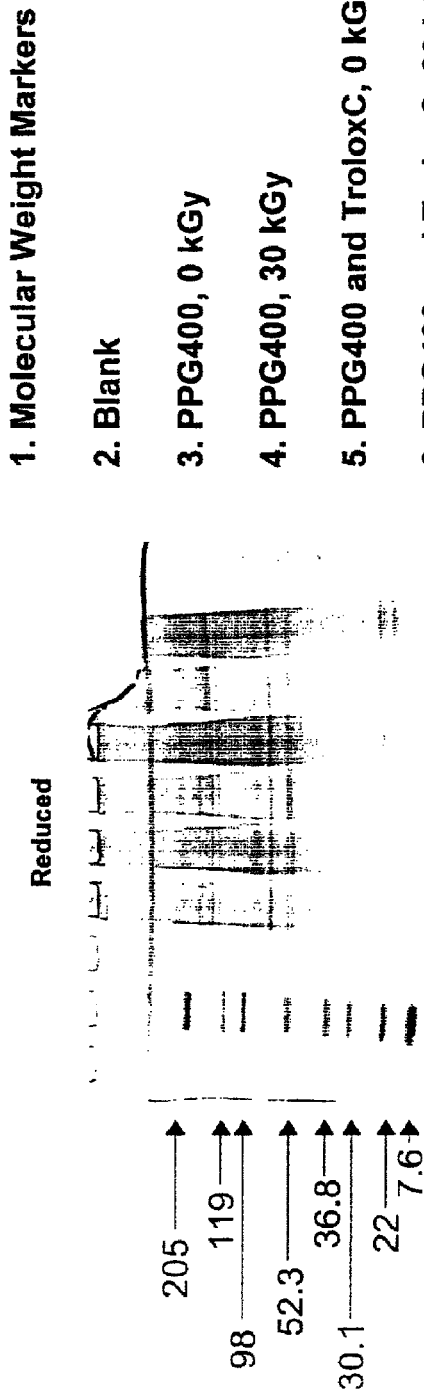

Results:
The HPLC results are shown in FIGS. 4A-4C. In the presence of PPG 400, the results were nearly identical whether the heart valve had been irradiated or not. The addition of a single stabilizer (trolox C) or a stabilizer mixture produced even more effective results. The gel analysis, shown in FIG. 4D, confirmed the effectiveness of the protection provided by these conditions.

Example 6

In this experiment, the effects of gamma irradiation were determined on porcine heart valve cusps in the presence of 50% DMSO and, optionally, a stabilizer, and in the presence of polypropylene glycol 400 (PPG400).

Preparation of Tissue for Irradiation:
1. 5 vials of PV and 3 vials of atrial valves (AV) were thawed on ice.
2. Thaw media was removed and valves rinsed in beaker filled with PBS.
3. Transferred each valve to 50 ml conical containing PBS. Washed by inversion and removed.
4. Repeated wash 3×.
5. Dissected out the 3 cusps (valves).
6. Stored in PBS in 2 ml screw top Eppendorf Vials (Eppendorfs) and kept on ice.

Preparation of Stabilizers:
All stabilizers were prepared so that the final concentration of DMSO is 50%.

1 M Ascorbate in 50% DMSO:
Aldrich cat# 26,855-0 lot# 10801HU 200 mg dissolved in 300 µl $H_2O$. Add 500 µl DMSO. The volumn was adjusted to 1 ml with $H_2O$ Final pH is ≈8.0

1 M Coumaric Acid:
Sigma cat# C-9008 lot# 49H3600. MW 164.2
Dissolve 34.7 mg in 106 µl DMSO, pH=≈3.0
138 µl $H_2O$ was added. Sample crashed out.
Coumaric went back into solution once pH was adjusted to 7.5 with 1 N NaOH.

1 M n-Propyl Gallate:
Sigma cat# P-3130 lot# 117H0526. MW 212.2
Dissolve 58.2 mg in 138 µl DMSO.
Add 138 µl $H_2O$. Final pH is 6.5 or slightly lower.

Stabilizer Mixture:
1.0 ml 500 mM Ascorbate
500 µl 1 M Coumaric Acid
300 µl 1 M n-propyl gallate
<u>1.2ml 50% DMSO</u>
3.0 ml Method:
1.6 ml of a solution (stabilizer mixture or PPG400) was added to each sample and then the sample was incubated at 4° C. for 25 days. Valves and 1 ml of the solution in which they were incubated were then transferred into 2 ml irradiation vials. Each sample was irradiated with gamma irradiation at a rate of 1.723 kGy/hr at 3.6° C. to a total dose of 25 kGy.

Hydrolysis of Tissue:
1. Washed each cusp 6× with acetone in a 2 ml Eppendorf Vial.
2. After final acetone wash, dried sample in Savant (without heat) for approximately 10-15 minutes or until dry.
3. Weighed the samples, transferred them to hydrolysis vials and then added 6 N HCl at a volume of 20 mg tissue/ml HCl:

| Sample ID | Dry Weight (mg) | µl 6 N HCl |
|---|---|---|
| 1. PBS/0 kGy | 11.4 | 570 |
| 2. PBS/25 kGy | 6.0 | 300 |
| 3. DMSO/0 kGy | 6.42 | 321 |
| 4. DMSO/25 kGy | 8.14 | 407 |
| 5. DMSO/SC-a/0 kGy | 8.7 | 435 |
| 6. DMSO/SC-a/25 kGy | 8.15 | 408 |
| 7. PPG/0 kGy | 13.09 | 655 |
| 8. PPG/25 kGy | 10.88 | 544 |

5. Samples were hydrolyzed at 110° C. for approximately 23 hours.

6. Hydrolysates were transferred into eppendorf vials and centrifuged at 12,000 rpm for 5 min.

7. Supernatent was transferred into a clean eppendorf vial.

8. 50 µl hydrolysate was diluted in 8 ml Nerl $H_2O$ (diluting HCl to approximately 37 mM).

9. Spiked in 200 µl of 2×int-pyd. Mixed by inversion. (For 2000 µl 2×int-pyd: 200 µl 20×int-pyd+1.8 ml Nerl $H_2O$.)

10. Samples were loaded onto SP-Sephadex C25 column (approximately 1×1 cm packed bed volume) that had been equilibrated in water. (Column was pre-charged with NaCl)

11. Loaded flow through once again over column.

12. Washed with 20 ml 150 mM HCl.

13. Eluted crosslinks with 5 ml 2 N HCl into a low binding tube. 50 ml 2 N HCl: 8.6 ml concentrated HCl adjusted to a volume of 50 ml with Nerl $H_2O$.

14. Dried entire sample in Savant.

Guanidine HCl Extraction and DEAE-Sepharose Purification of Proteoglycans:

4M Guanidine HCl Extraction:

1. Removed all three cusps from gamma irradiation vial and transferred to separate 50 ml conical tube.

2. Washed cusps five times with 50 ml dPBS (at 4° C. over approx. 5 hours) and determined wet weight of one cusp after damping on Kimwipe.

3. Transferred one cusp from each group to 1.5 ml microfuge tube and added appropriate volume of 4M guanidine HCl/150 mM sodium acetate buffer pH 5.8 with 2 µg/ml protease inhibitors (aprotinin, leupeptin, pepstatin A) to have volume to tissue ratio of 15 (see Methods in Enzymology Vol. 144 p. 321—for optimal yield use ratio of 15 to 20).

4. Diced cusps into small pieces with scissors.

5. Nutated at 4° C. for ~48 hours.

6. Centrifuged at 16,500 RPM on Hermle Z-252M, 4° C.×10 min.

7. Collected guanidine soluble fraction and dialyze against PBS in 10K MWCO Slide-A-Lyzer overnight against 5 L PBS (3 slide-a-lyzers with one 5 L and 5 slide-a-lyzers in another 5 L) to remove guanidine.

8. Changed PBS and dialyzed for additional 9 hours at 4° C. with stirring.

9. Collected the dialysate and store at 4° C.

10. Centrifuged at 16,500 RPM on Hermle Z-252M, 4° C.×5 min

11. Removed PBS soluble fraction for DEAE-Sepharose chromatography.

DEAE-Sepharose Chromatography

1. Increase the NaCl concentration of 500 µl of PBS soluble guanidine extract to 300 mM NaCl (Assumed PBS soluble fractions were already at ~150 mM NaCl, so added 15 µl 5M NaCl stock to each 500 µl sample).

2. Equilibrated ~1 ml of packed DEAE-Sepharose (previously washed with 1M NaCl/PB pH 7.2) into 300 mM NaCl/PB pH 7.2 (Note: To make 300 mM NaCl/PB pH7.2—added 3 ml of 5M NaCl stock to 100 ml PBS).

3. Added 200 µl of 1:µl slurry of resin to 515 µL of GuHCl extracts (both at 300 mM NaCl).

4. Nutated at ambient temperature for ~one hour.

5. Centrifuged gently to pellet resin.

6. Removed "unbound" sample and stored at −20° C.

7. Washed resin 5 times with ~1.5 ml of 300 mM NaCl/PBS pH7.2.

8. After last wash, removed all extra buffer using a 100 µl Hamilton syringe.

9. Eluted at ambient temperature with three 100 µl volumes of 1M NaCl/PB pH 7.2. Stored at −20° C.

SDS-PAGE:

5-20% gradient gels for analysis of PBS soluble Guanidine HCl extracts and DEAE-Sepharose chromatography.

1. Gel#1: GuHCl extracts/PBS soluble fractions—Toluidine blue and then Coomassie blue stained.

2. Gel#2: DEAE-Sepharose Eluant Fraction#1—Toluidine Blue stained then Coomassie Blue stained.

Quantification of Collagen Crosslinks by HPLC:

1. Prepare 100-200 µl 1× solution in 1% heptafluorobutyric acid (HFBA).

2. Inject 50 µl on C18 HPLC column equilibrated with mobile phase.

3. Spectrofluorometer is set for excitation at 295 nm and emission at 395 nm.

4. Calculate the integrated fluorescence of Internal-Pyridinoline (Int-Pyd) per 1 µl of 1× solution of Int-Pyd.

Figure 5A:
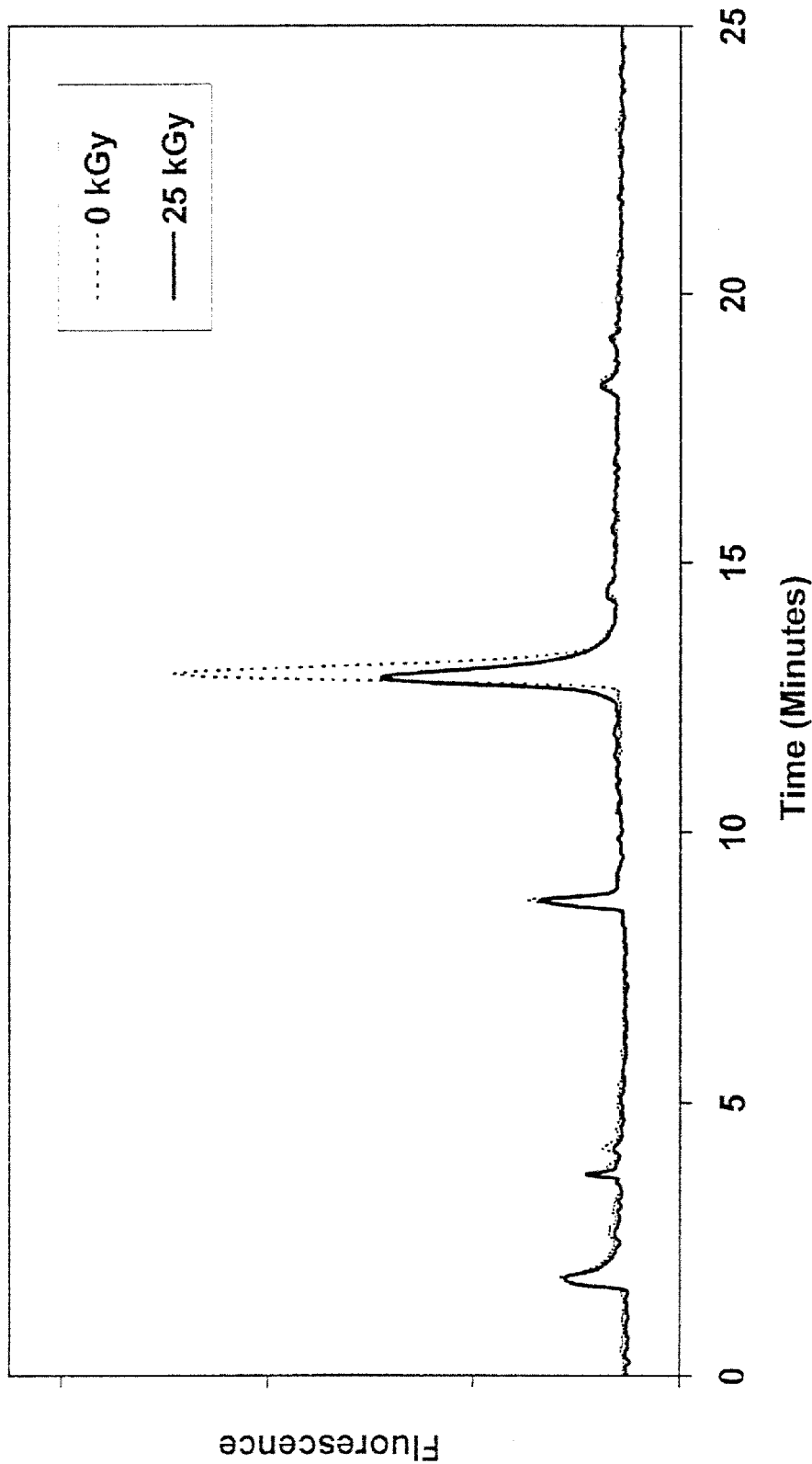
FIGS. 5(a)-5(e) show the effects of gamma irradiation on porcine heart valve cusps in the presence of 50% DMSO and, optionally, a stabilizer, and in the presence of polypropylene glycol 400 (PPG400).
Figure 5B:
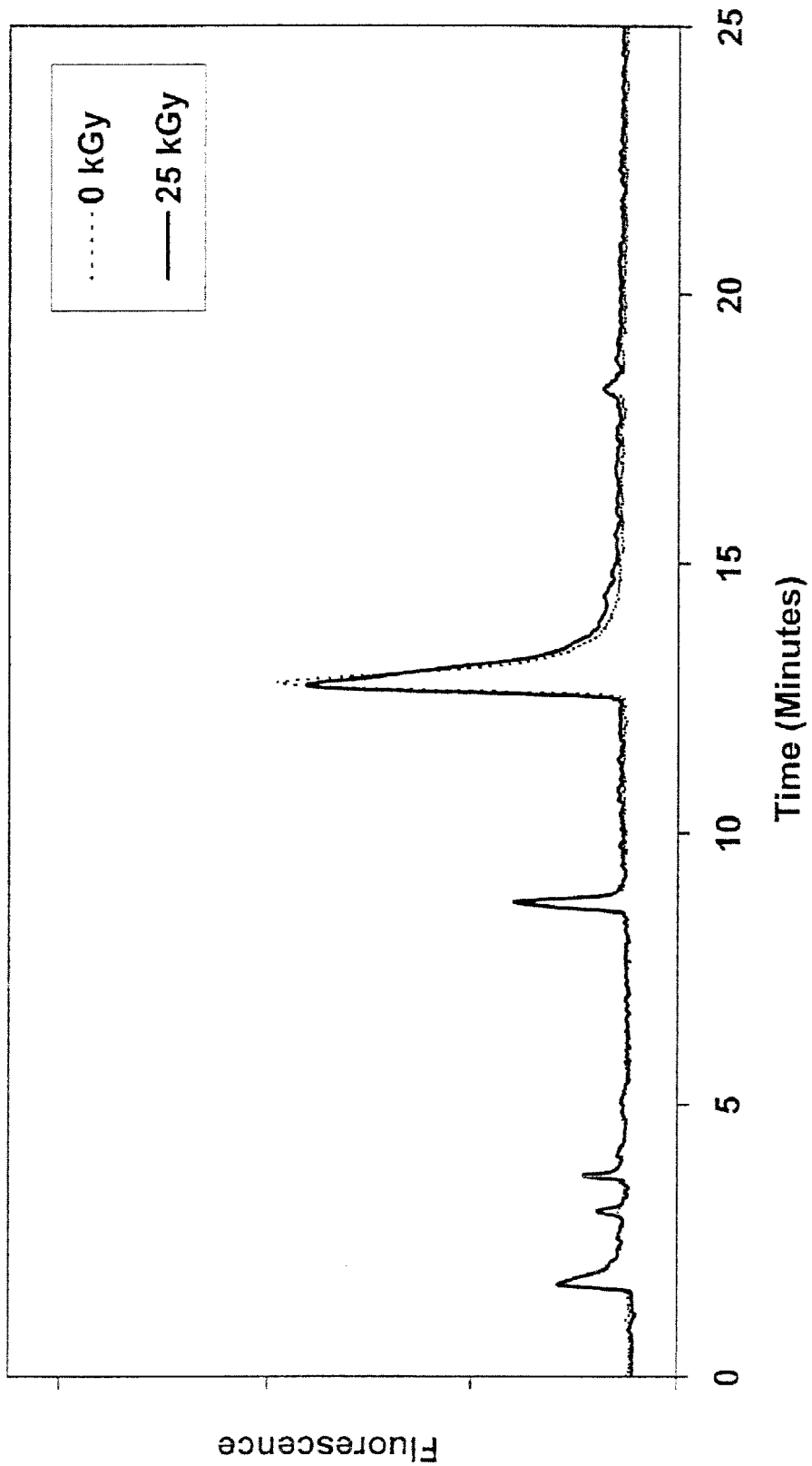
Figure 5C:
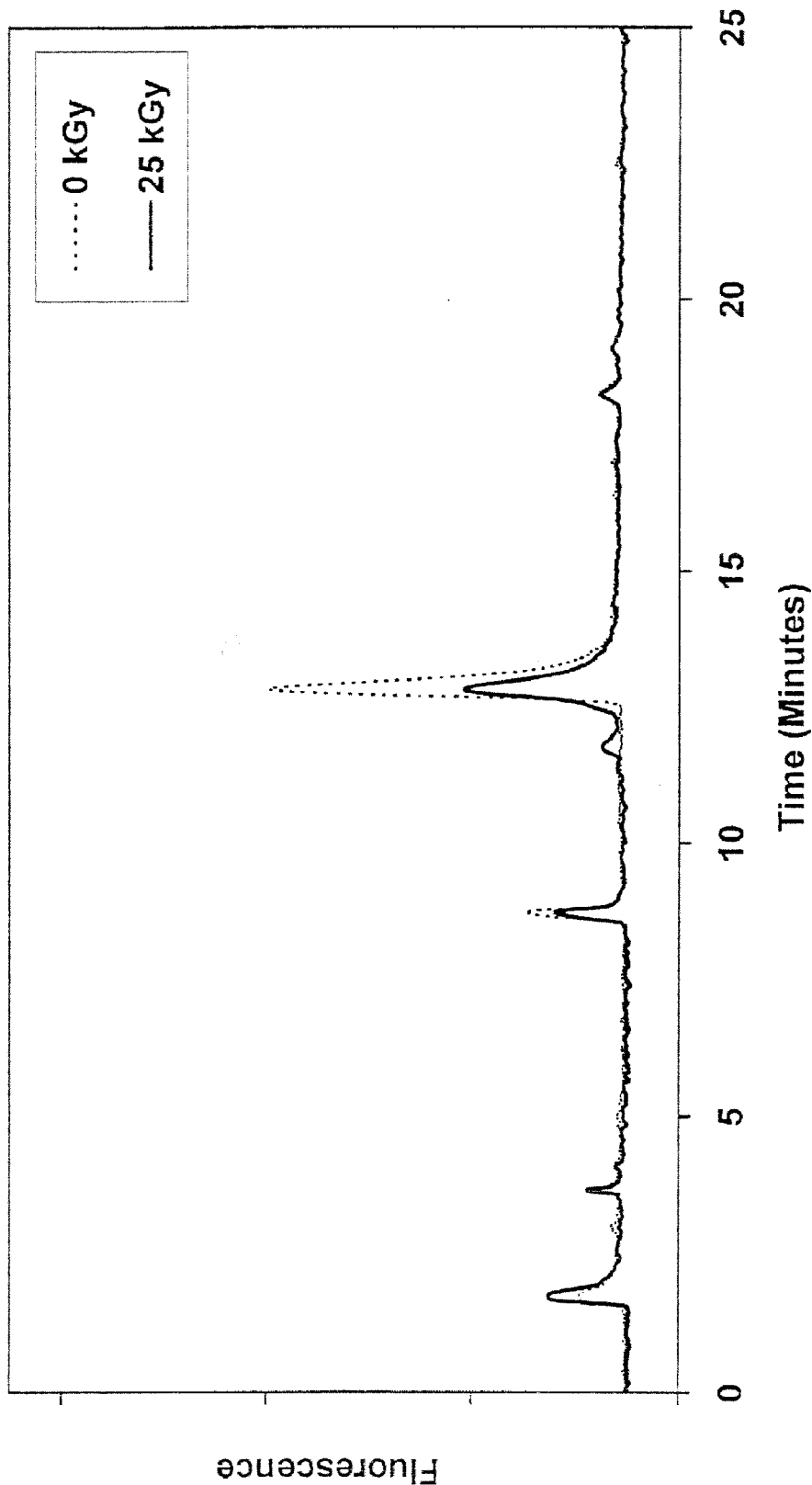
Figure 5D:
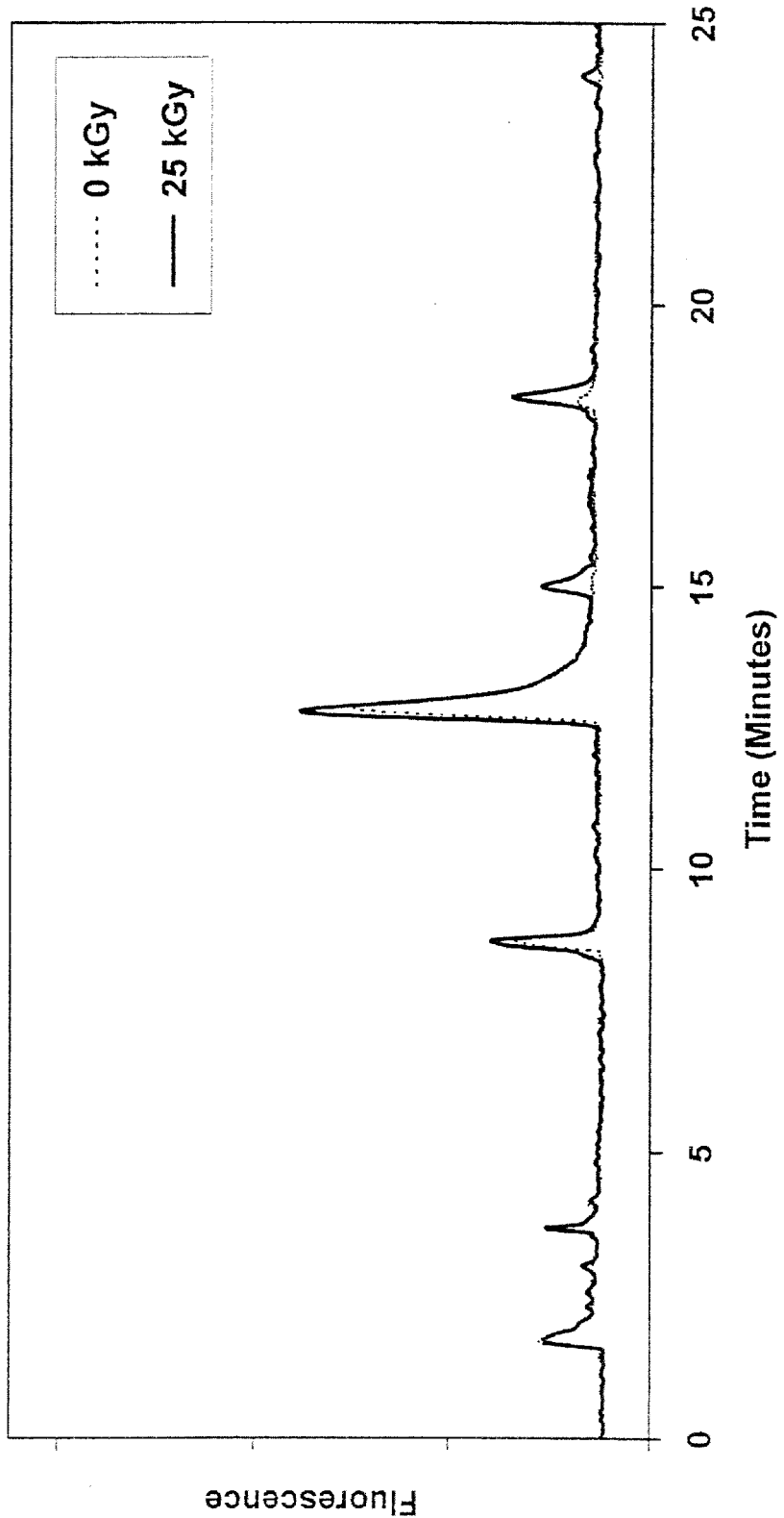
Figure 5E:
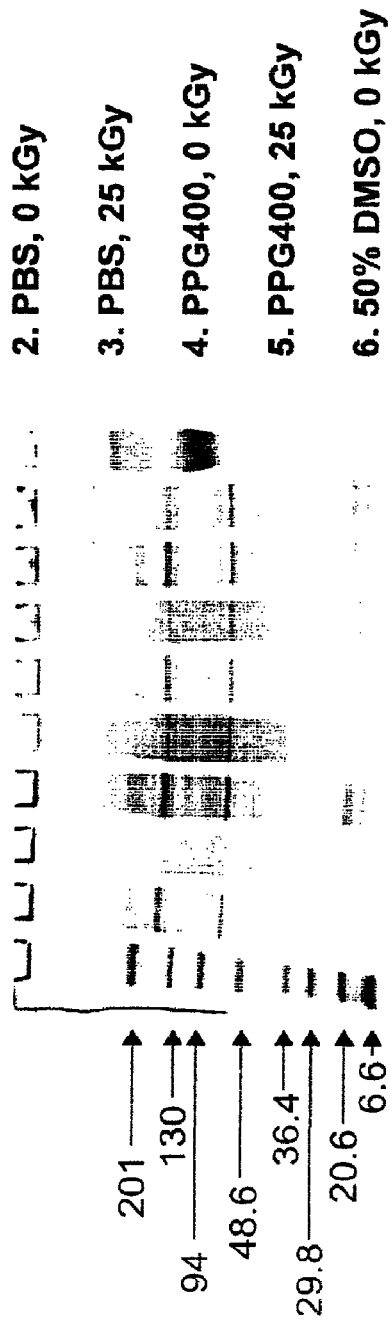

Results:

The HPLC results are shown in FIGS. 5A-D. The major peak represents the Internal-Pyridinoline (int-Pyd) peak. Irradiation in an aqueous environment (PBS) produced pronounced decreases in the smaller peaks (FIG. 5A). Reduction of the water content by the addition of a non-aqueous solvent (PPG 400) produced a nearly superimposable curve (FIG. 5B). DMSO was less effective (FIG. 5C), while DMSO plus a mixture of stabilizers (FIG. 5D) was more effective at preserving the major peak although some minor peaks increased somewhat. The area under the pyd peak for each sample was calculated as shown in the table below. These results confirm the above conclusions and show that the amino acid crosslinks (pyd) found in mature collagen are effectively conserved in the samples containing PPG and DMSO with a scavenger mixture. Gel analysis is shown in FIG. 5E and reflects the major conclusions from the HPLC analysis, with significant loss of bands seen in PBS and retention of the major bands in the presence of non-aqueous solvents.

| Sample | Area of Pyd Peak |
| --- | --- |
| PBS/0 kGy | 94346 |
| PBS/25 kGy | 60324 |
| DMSO/0 kGy | 87880 |
| DMSO/25 kGy | 49030 |
| DMSO/SCa/0 kGy | 75515 |
| DMSO/SCa/25 kGy | 88714 |
| PPG/0 kGy | 99002 |
| PPG/25 kGy | 110182 |

Example 7

In this experiment, frozen porcine AV heart valves soaked in various solvents were gamma irradiated to a total dose of 30 kGy at 1.584 kGy/hr at −20° C.

Materials:

1. Porcine heart valve cusps were obtained and stored at −80° C. in a cryopreservative solution (Containing Fetal calf serum, Penicillin-Streptomycin, M199 media, and approximately 20% DMSO).

2. Dulbecco's Phosphate Buffered Saline: Gibco BRL cat#14190-144 lot 1095027

3. 2 ml screw cap vials: VWR cat# 20170-221 lot #0359

4. 2 ml glass vials: Wheaton cat# 223583 lot#370000-01

5. 13 mm stoppers: Stelmi 6720GC lot#G006/5511
    6. DMSO: JT Baker cat# 9224-01 lot# H406307. Sodium ascorbate: Aldrich cat#26,855-0 lot 10801HU; prepared as a 2M stock in Nerl water.
    8. Fetal calf serum
    9. Penicillin-Streptomycin
    10. M199 media
    11. DMSO Methods:

Cryopreservative Procedure:

Preparation of Solutions:
    Freeze Medium:
    Fetal calf serum (FCS) (10%)=50 ml
    Penicillin-Streptomycin=2.5 ml
    M199=QS500 ml
    2M DMSO
    DMSO=15.62 g
    Freeze Medium=QS 100 ml
    3M DMSO
    DMSO=23.44 g
    Freeze Medium=QS 100 ml
    1. Place dissected heart valves (with a small amount of conduit/muscle attached) into glass freezing tubes (label with pencil).
    2. Add 2 ml of freeze medium.
    3. At 21° C., add 1 ml 2M DMSO solution.
    4. At 5 minutes, add 1 ml 2M DMSO solution.
    5. At 30 minutes, add 4 ml 3M DMSO solution.
    6. At 45 minutes and 4° C., place freezing tubes on ice.
    7. At 50 minutes and −7.2° C., seed bath.
    8. At 55 minutes and −7.2° C., nucleate.
    9. At 70 minutes, cool to −40° C. at 1° C./minute. Remove from bath and place in canister of $LN_2$, and store in cryogenic storage vessel.

Procedure for Irradiation of Heart Valves:
    1. Thawed AV heart valve cusps on wet ice.
    2. Pooled cusps into 50 ml tubes.
    3. Washed cusps with ~50 ml dPBS at 4° C. while nutating. Changed PBS 5× over the course of 5 hrs.
    4. Transferred cusps into 2 ml screw cap tubes (2 cusps/tube).
    5. Added 1.0 ml of the following to two of each of two tubes: dPBS, 50% DMSO and 50% DMSO with 200 mM sodium ascorbate (2M sodium ascorbate stock was diluted as follows: 400 µl (2M)+1.6 ml water+2 ml 100% DMSO).
    6. Incubated tubes at 4° C. with nutating for ~46 hours.
    7. Transferred solutions and cusps to glass 2 ml vials, stoppered and capped.
    8. All vials were frozen on dry ice.
    9. Frozen samples were then irradiated at −20° C. at a rate of 1.584 kGy/hr to a total dose of 30 kGy.

Figure 6A:
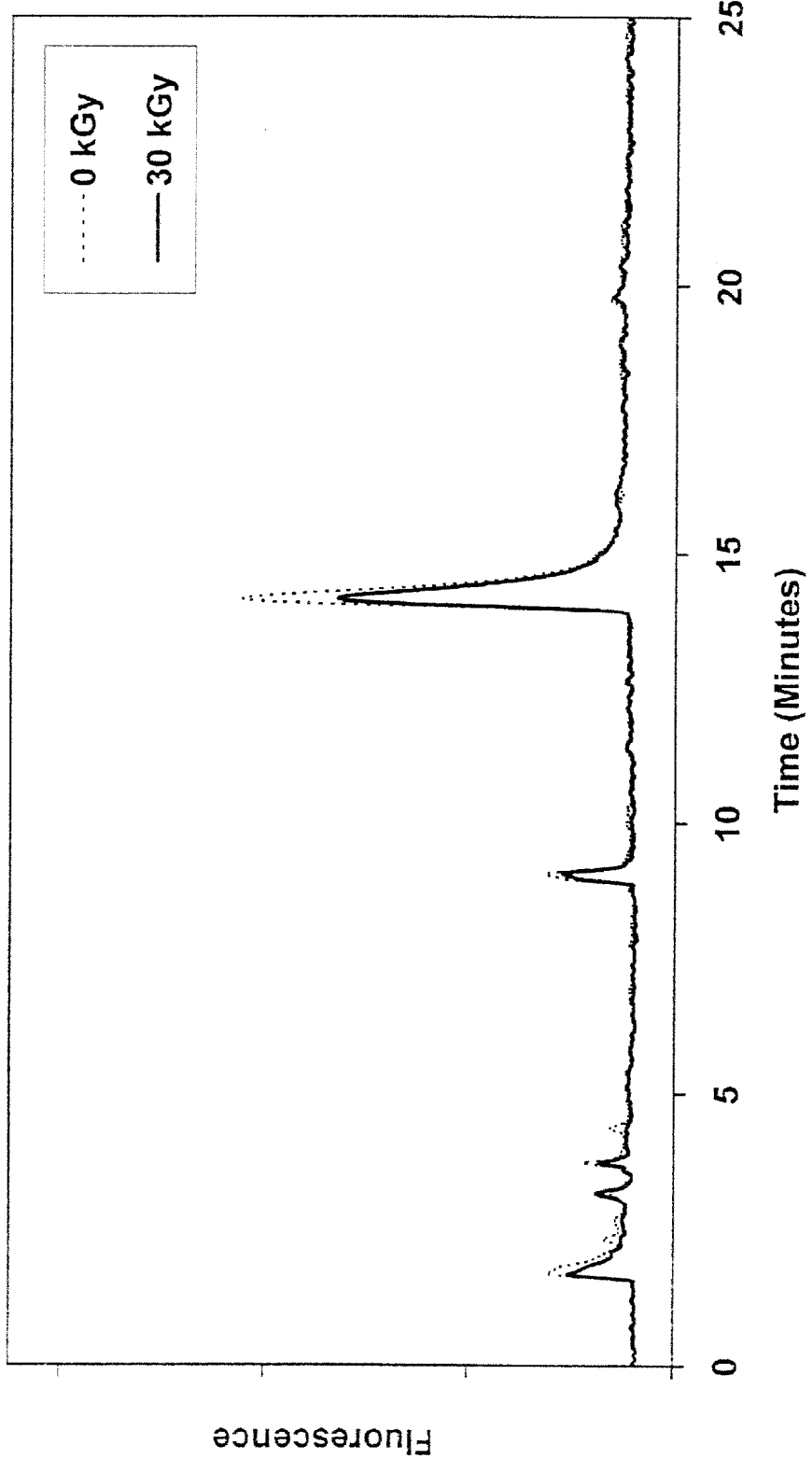
FIGS. 6(a)-6(e) show the effects of gamma irradiation on frozen porcine AV heart valves soaked in various solvents and irradiated to a total dose of 30 kGy at 1.584 kGy/hr at −20° C.
Figure 6B:
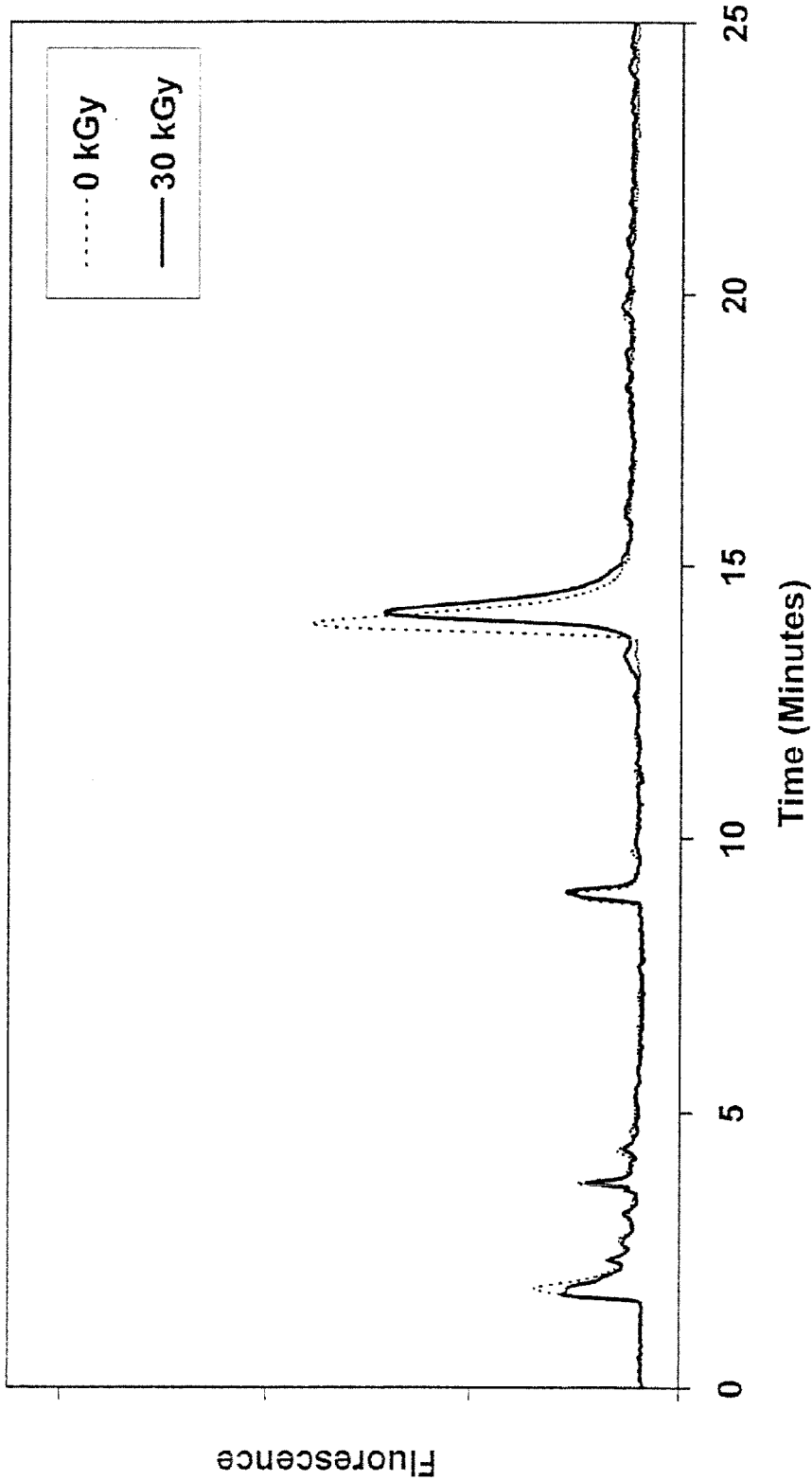
Figure 6C:
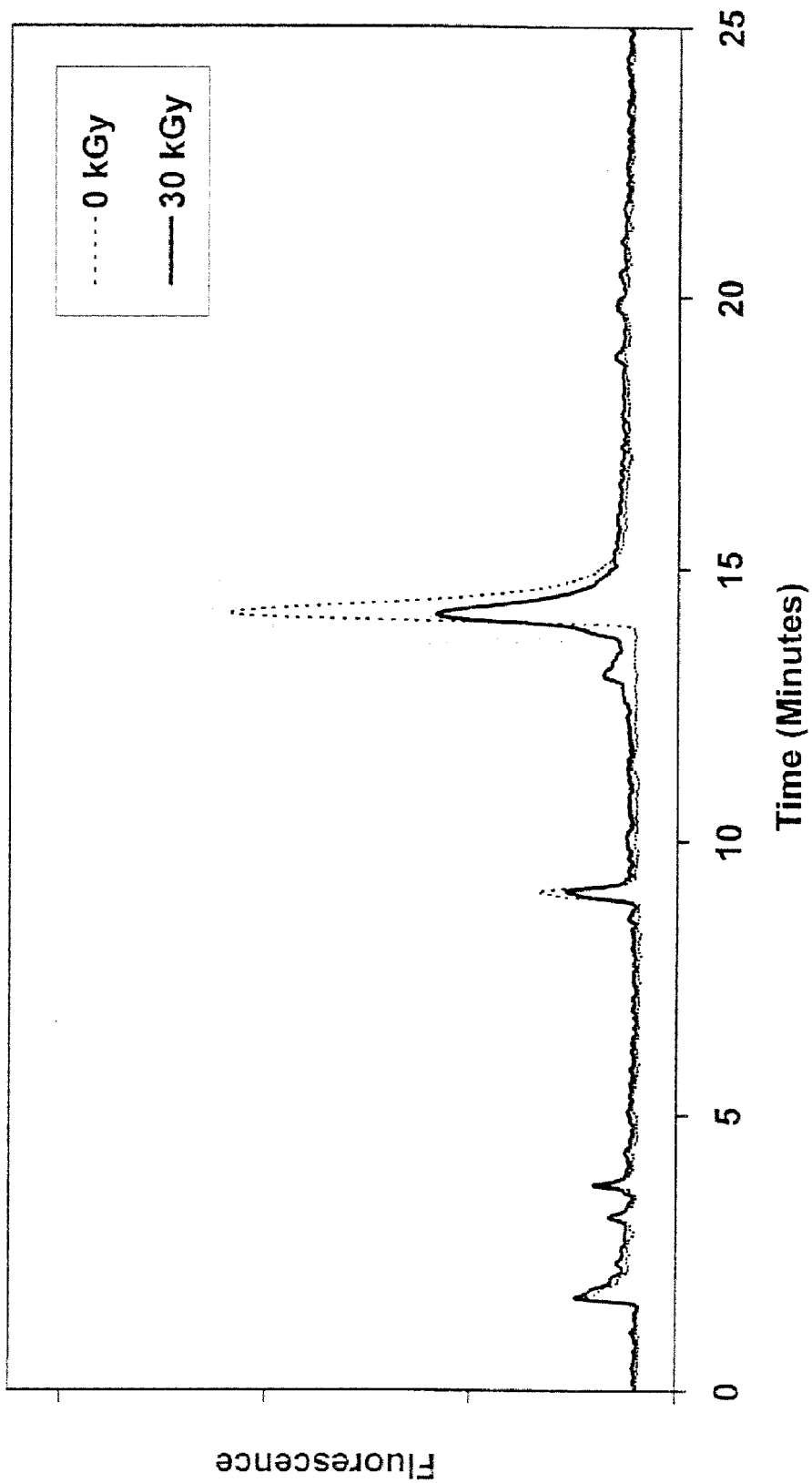
Figure 6D:
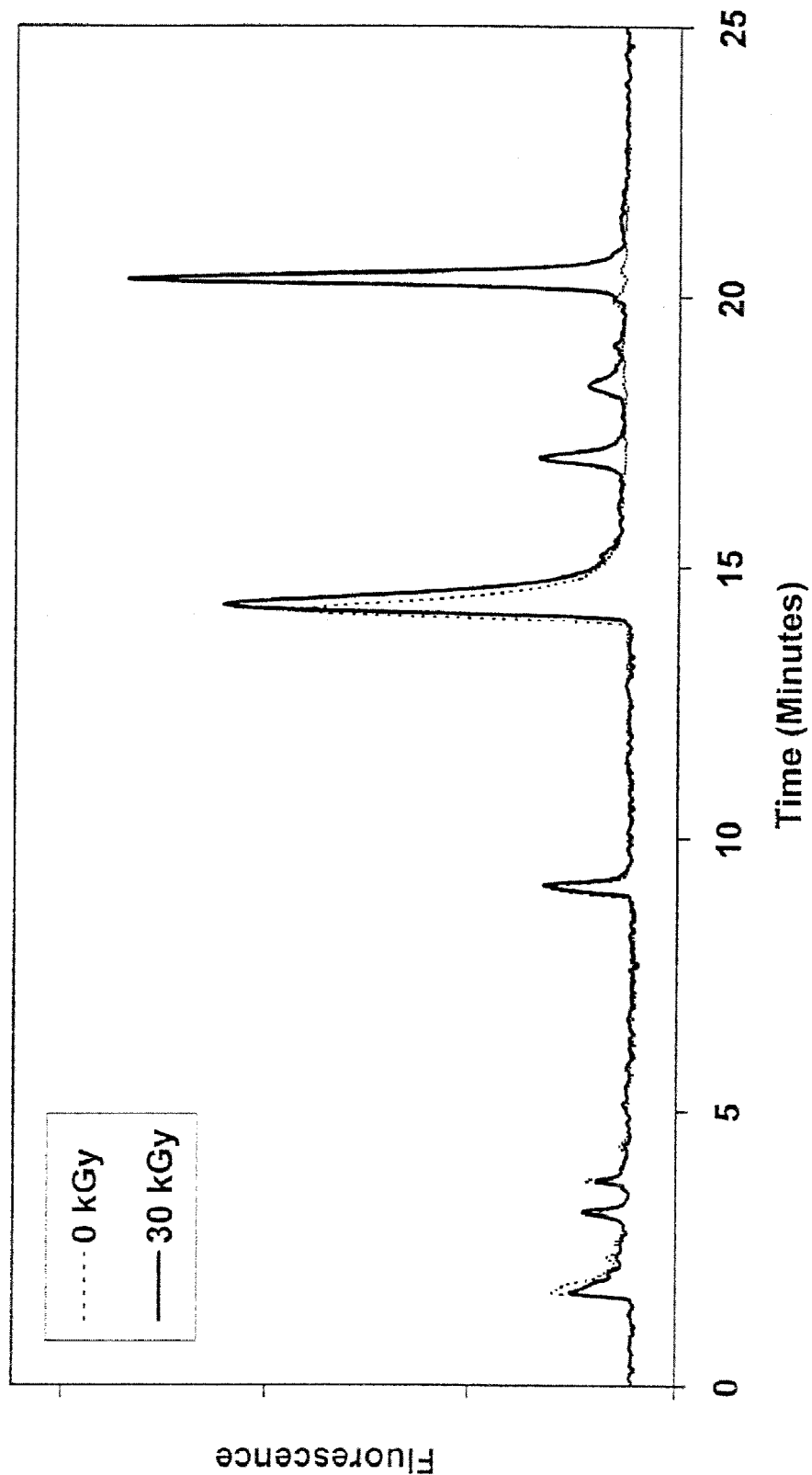
Figure 6E:
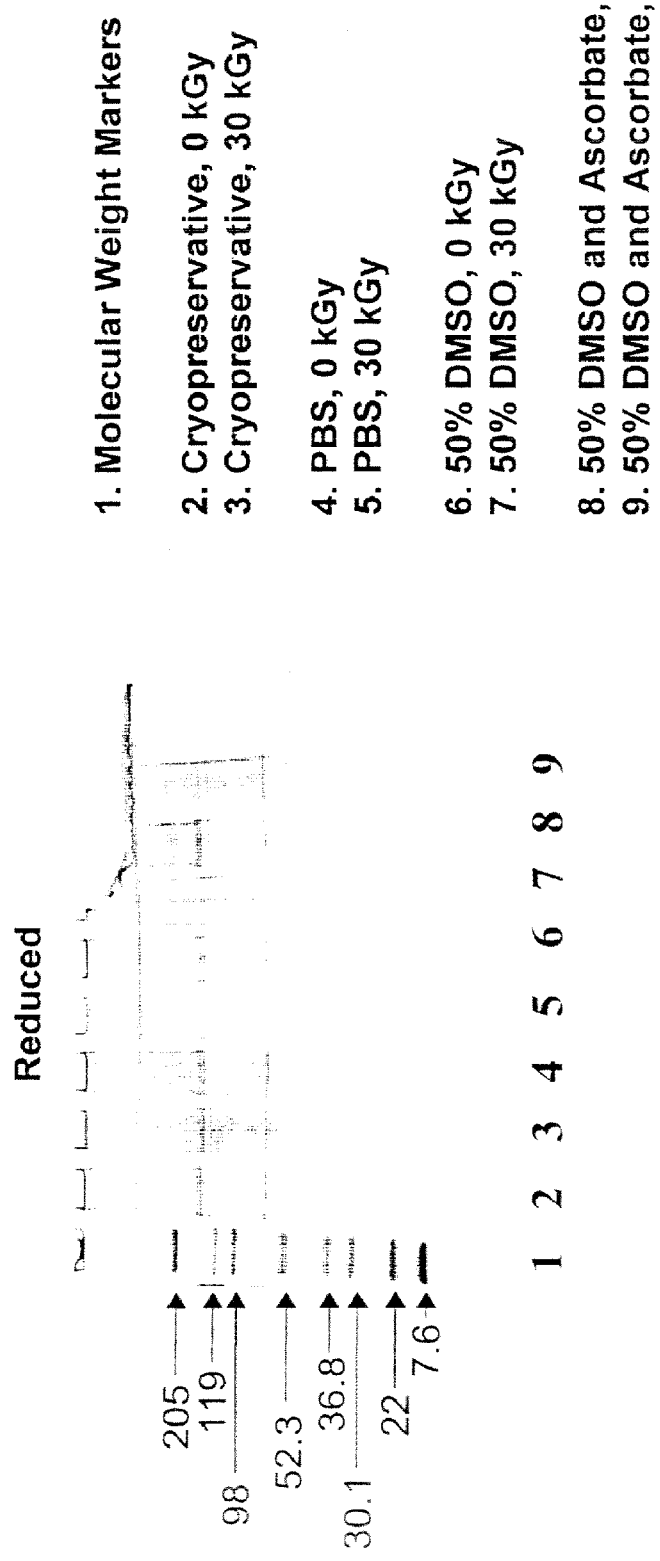

Results:

The results of the HPLC analysis are shown in FIGS. 6A-6D. Irradiation in an aqueous environment (PBS) produced decreases in the smaller peaks (FIG. 6A). Reduction of the water content by the addition of a non-aqueous solvent (20% DMSO) reproduced these peaks more faithfully (FIG. 6B). Increasing the DMSO concentration to 50% was slightly more effective (FIG. 6C), while DMSO plus a mixture of stabilizers (FIG. 6D) was very effective at preserving both the major and minor peaks (the additional new peaks are due to the stabilizers themselves). Gel analysis is shown in FIG. 6E and reflects the major conclusions from the HPLC analysis, with significant loss of bands seen in PBS and retention of the major bands in the presence of non-aqueous solvents with and without stabilizers.

Example 8

In this experiment, frozen porcine AV heart valves soaked in various solvents were gamma irradiated to a total dose of 45 kGy at approximately 6 kGy/hr at −70° C.

Materials:
    1. Porcine heart valve cusps were obtained and stored at −80° C. in a cryopreservative solution (Same solution as that in Example 7).
    2. Dulbecco's Phosphate Buffered Saline: Gibco BRL cat#14190-144 lot 1095027
    3. 2 ml screw cap vials: VWR cat# 20170-221 lot #0359
    4. 2 ml glass vials: Wheaton cat# 223583 lot#370000-01
    5. 13 mm stoppers: Stelmi 6720GC lot#G006/5511
    6. DMSO: JT Baker cat# 9224-01 lot# H40630
    7. Sodium ascorbate: Aldrich cat# 26,855-0 lot 10801HU; prepared as a 2M stock in Nerl water.
    8. Polypropylene glycol 400 (PPG400): Fluka cat#81350 lot#386716/1

Methods:

Cryopreservative Procedure is the Same as that Shown in Example 7.
    1. Thawed AV heart valve cusps on wet ice. Dissected out cusps and washed the pooled cusps 6× with cold PBS.
    2. Dried each cusp and transferred cusps into 2 ml screw cap tubes (2 cusps/tube).
    3. Added 1.2 ml of the following to two of each of two tubes: dPBS, dPBS with 200 mM sodium ascorbate, PPG400, PPG400 for rehydration, 50% DMSO and 50% DMSO with 200 mM sodium ascorbate (2M sodium ascorbate stock was diluted as follows: 400 µl (2M)+1.6 ml water+2 ml 100% DMSO).
    4. Incubated tubes at 4° C. with nutating for ~46 hours.
    5. Replaced all solutions with fresh (with the following exception: for one PPG400 set, PPG400 was removed, the cusp washed with PBS+200 mM ascorbate, which was then removed and replaced with fresh PBS+200 mM ascorbate).
    6. Incubated tubes at 4° C. with nutating for ~46 hours.
    7. Changed the solution on the PPG400 dehyd./PBS+ascorbate rehydration cusps prepared in step 5).
    8. Incubated tubes at 4° C. with nutating for ~6 hours.
    9. Transferred solutions and cusps to glass 2 ml vials, stoppered and capped.
    10. All vials were frozen on dry ice.
    11. Frozen samples were then irradiated at −70° C. at a rate of 6 kGy/hr to a total dose of 45 kGy.

Figure 7A:
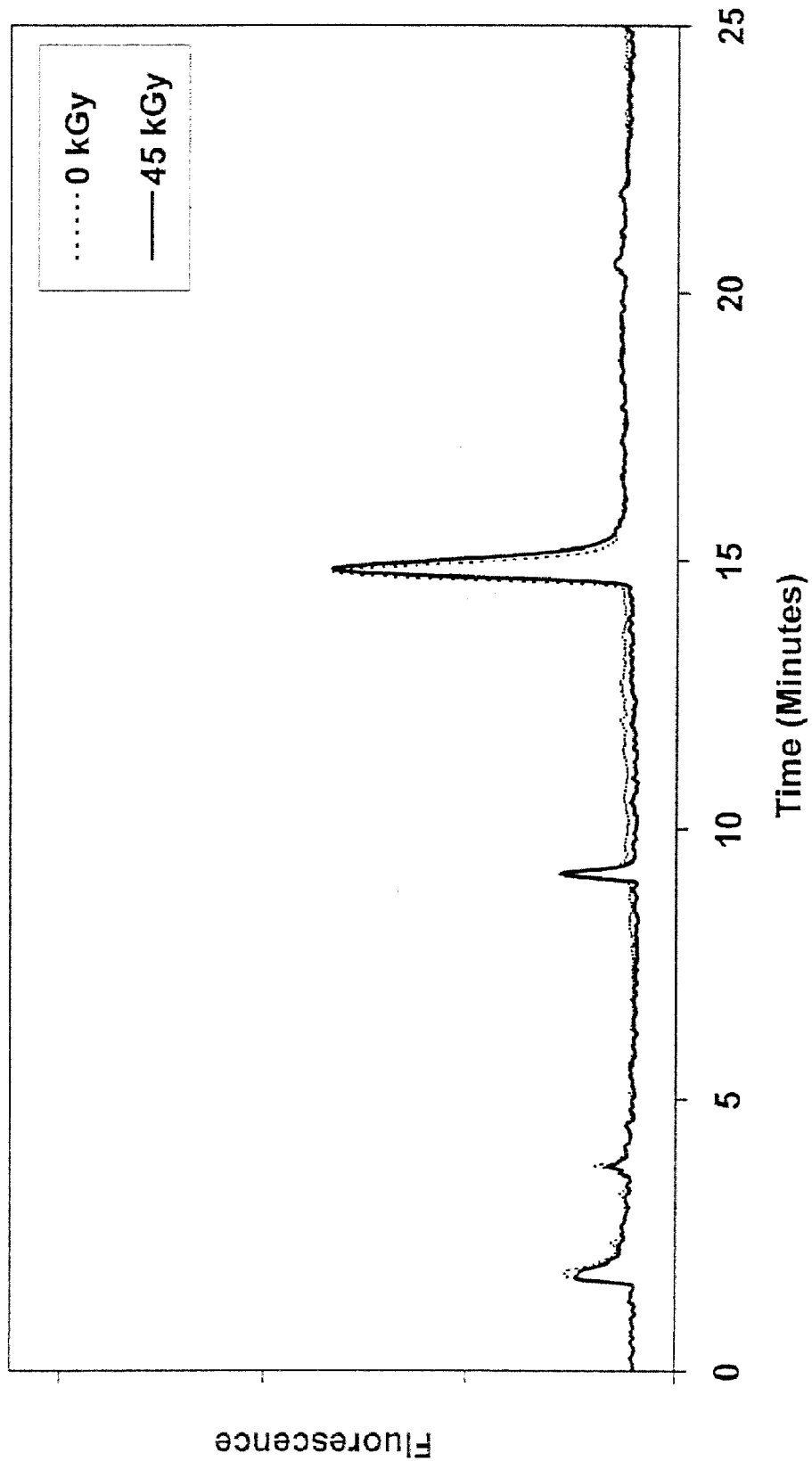
FIGS. 7(a)-7(h) show the effects of gamma irradiation on frozen porcine AV heart valves soaked in various solvents and irradiated to a total dose of 45 kGy at approximately 6 kGy/hr at −70° C.
Figure 7B:
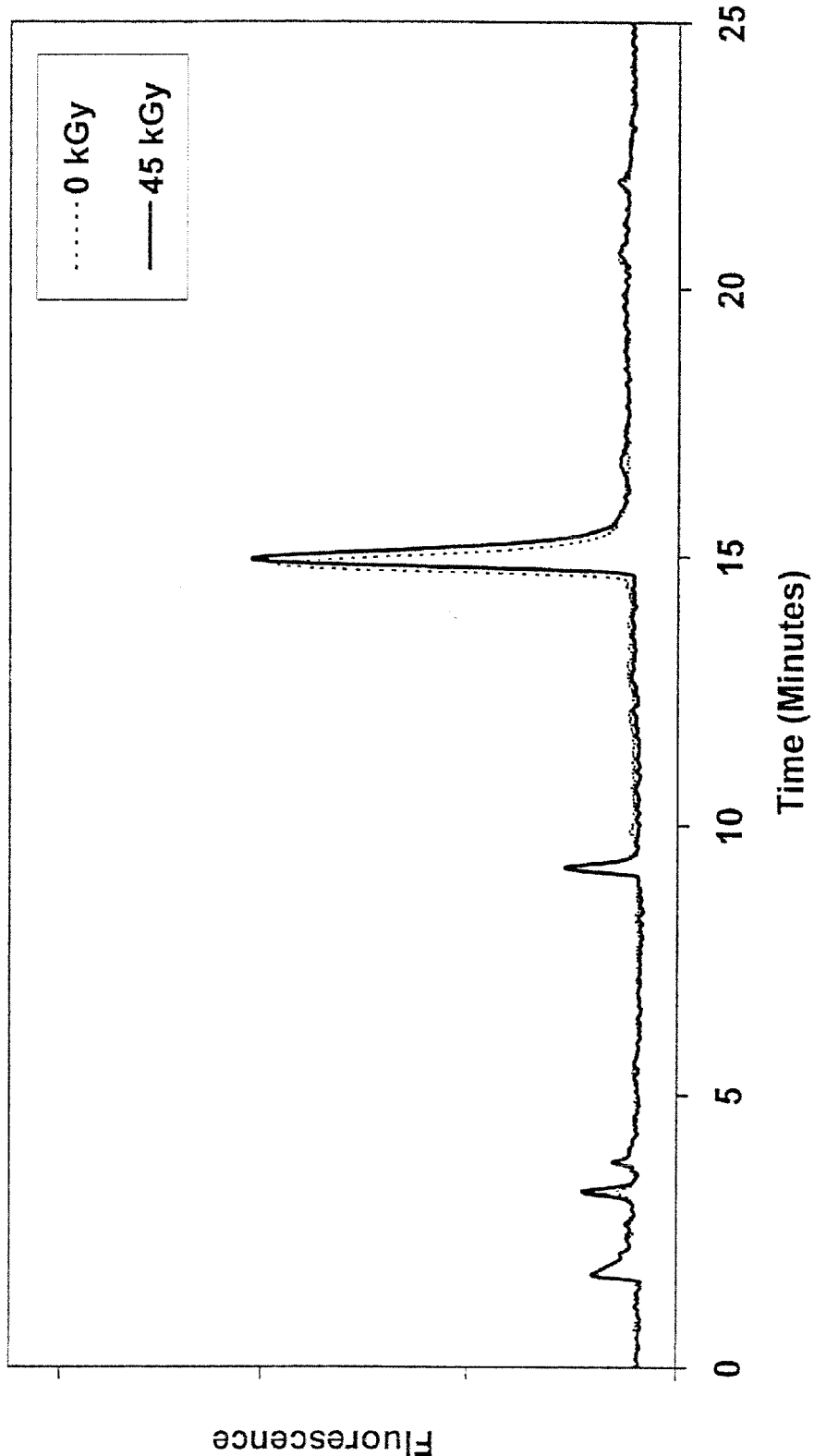
Figure 7C:
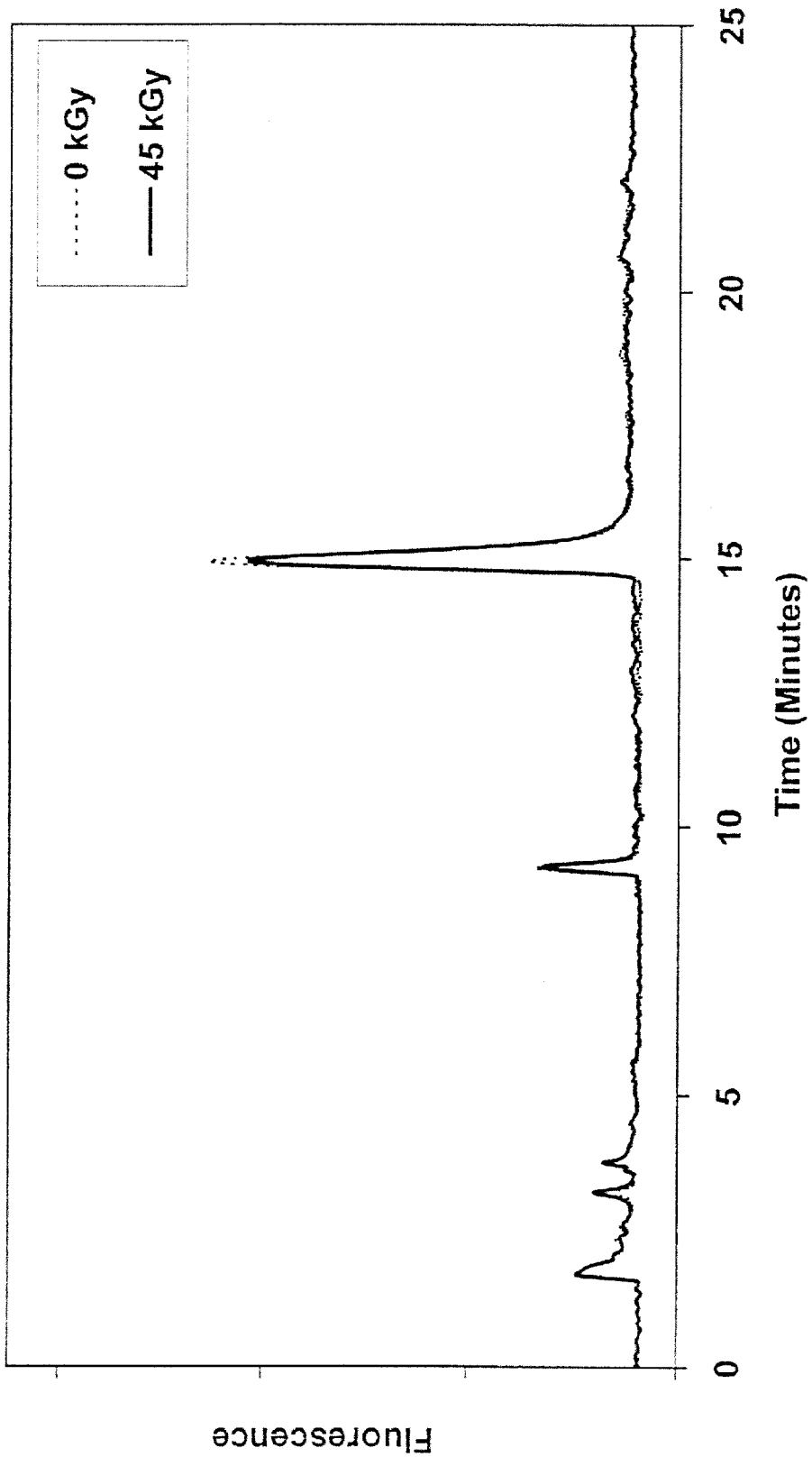
Figure 7D:
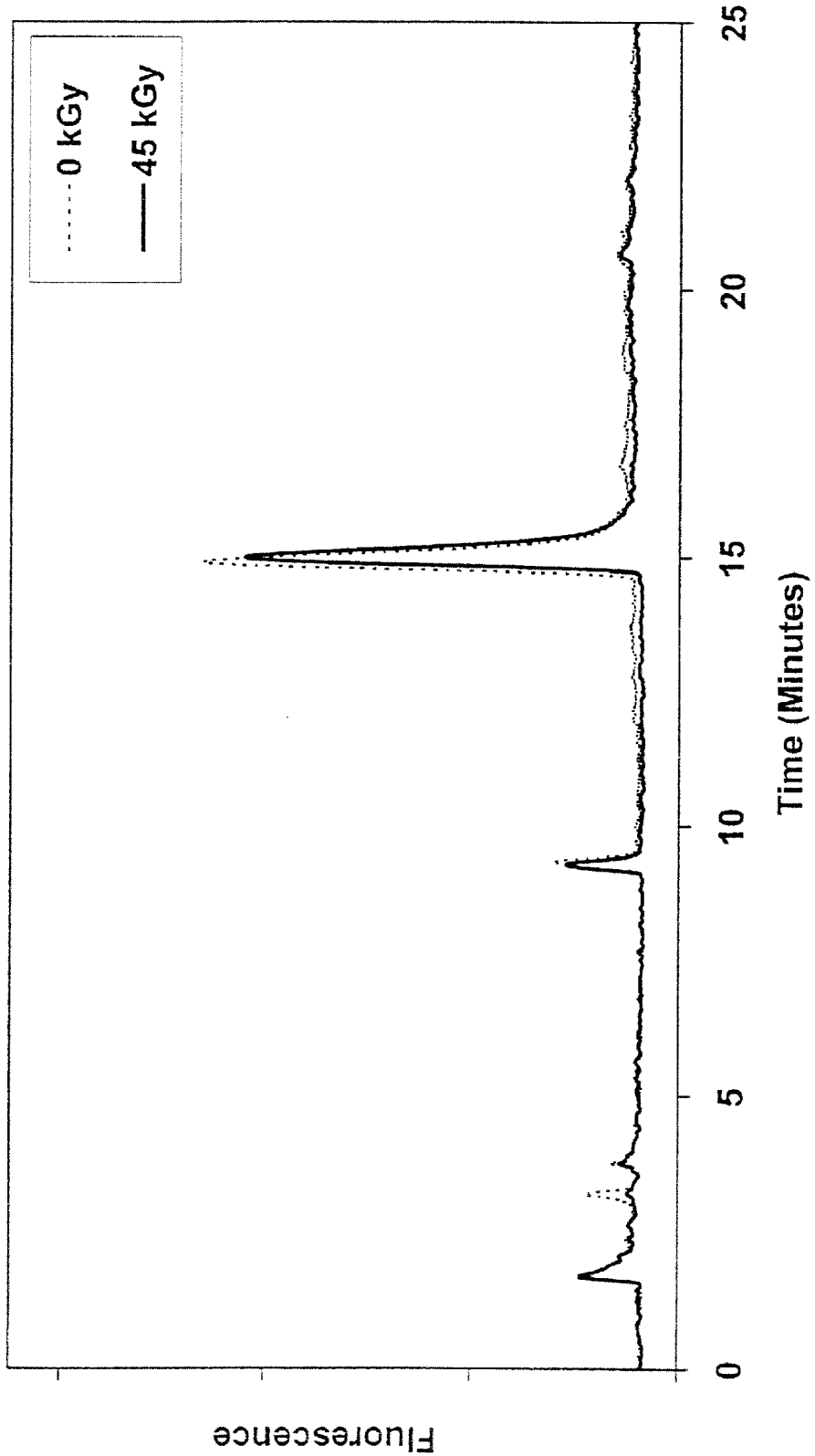
Figure 7E:
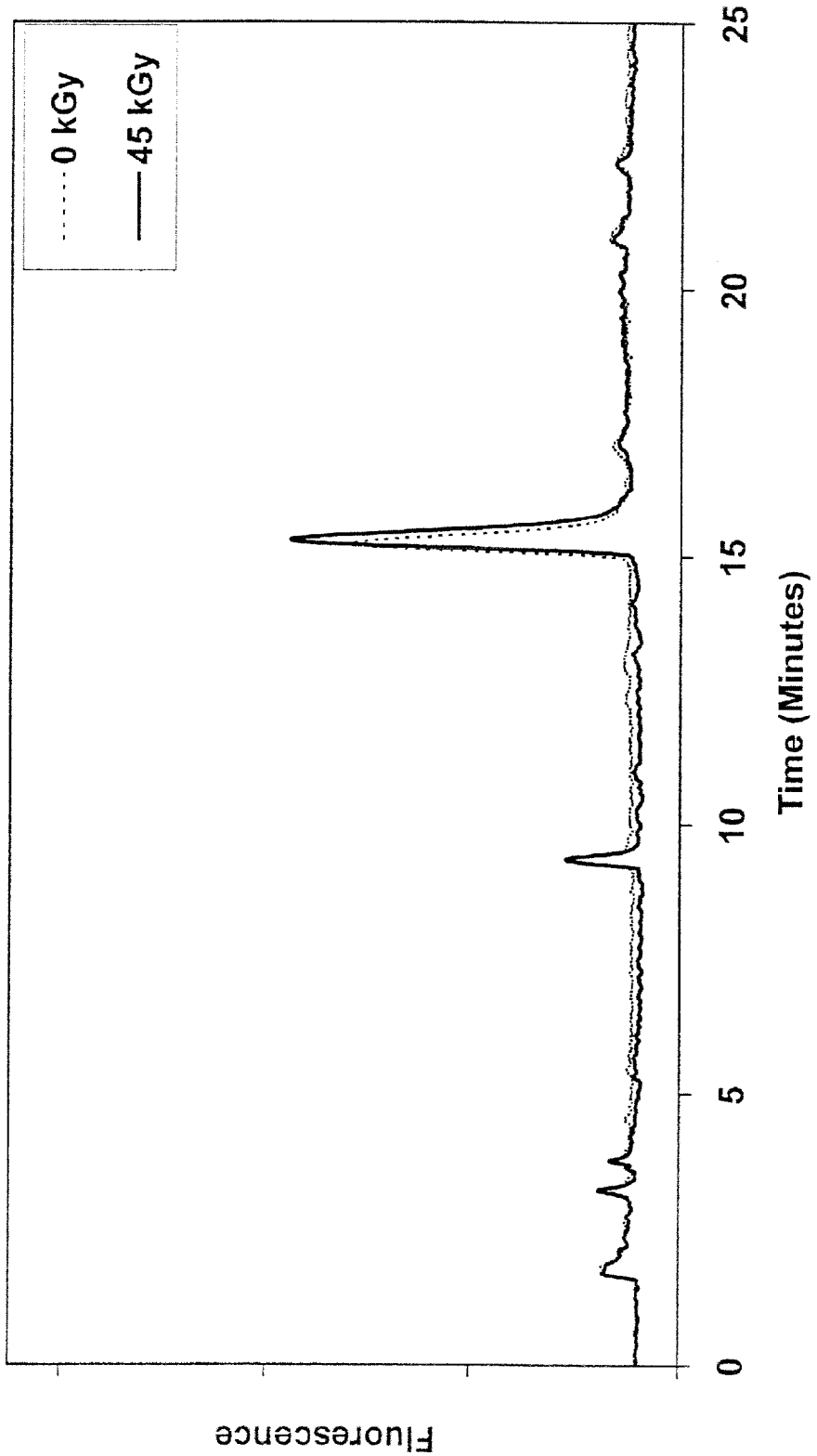
Figure 7F:
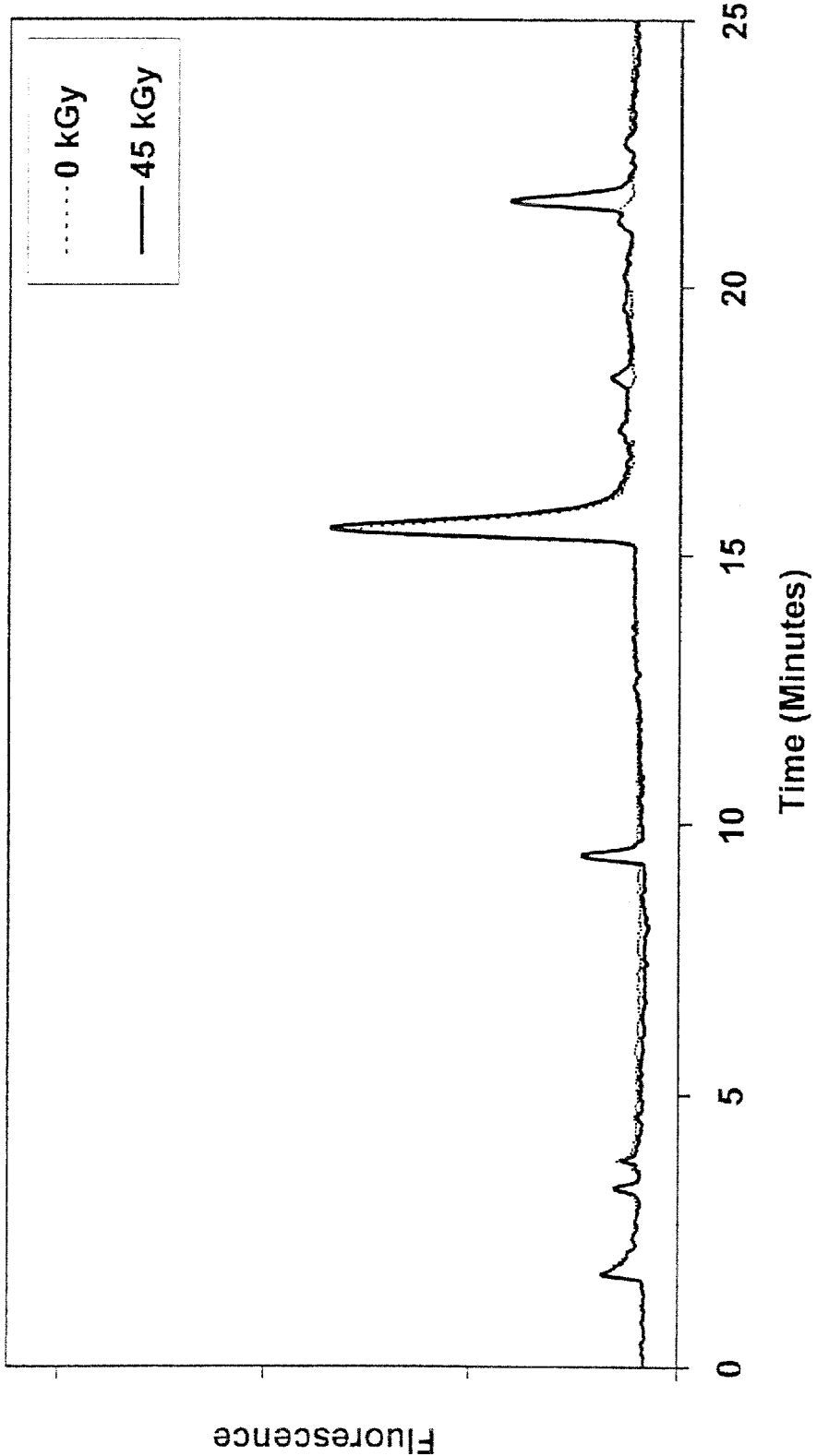
Figure 7G:
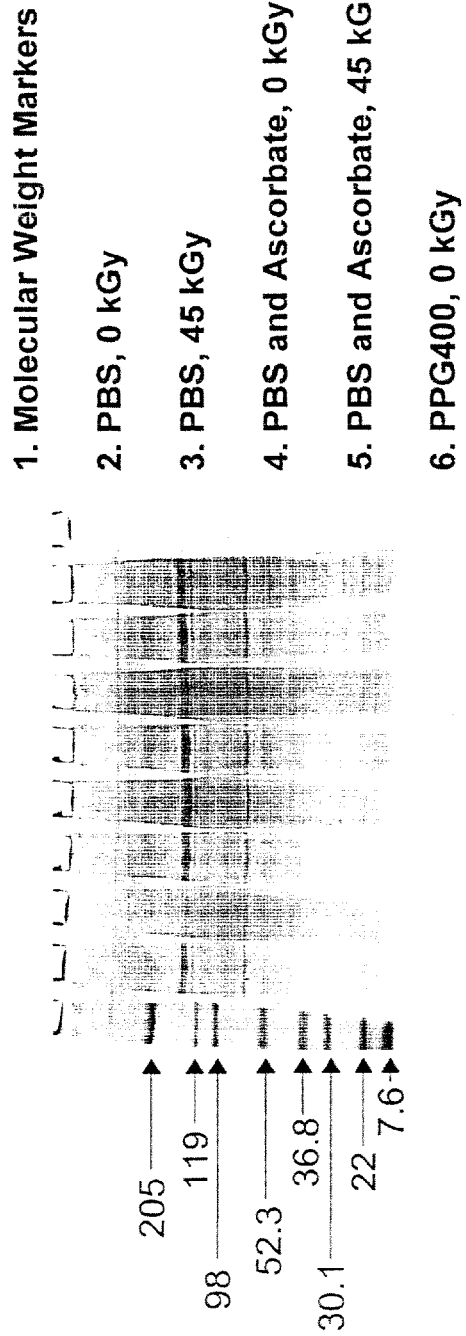
Figure 7H:
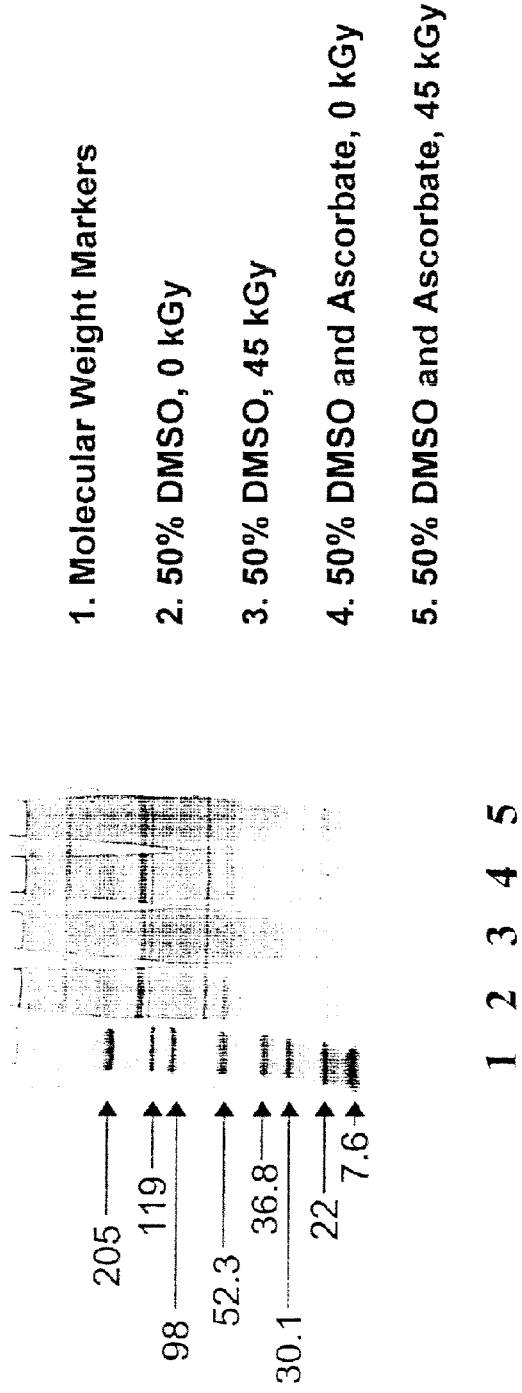

Results:

The results of the HPLC analysis are shown in FIGS. 7A-7F. Irradiation in an aqueous environment (PBS) resulted in changes in the minor peaks and a right shift in the major peak. The inclusion of various non-aqueous solvents, reduction in residual water, and the addition of stabilizers produced profiles that more closely matched those of the corresponding controls. The gel analysis is shown in FIGS. 7G-7H and shows a significant loss of bands in PBS, while the other groups demonstrated a significant retention of these lost bands.

When comparing the results from Example 8 to the results from Examples 5, 6, and 7, it becomes apparent that lowering the temperature for the gamma irradiation usually results in a decrease in the amount of modification or damage to the collagen crosslinks. One illustration of this temperature dependence is the sample containing 50% DMSO and ascorbate, in which the additional peaks are markedly decreased as the temperature is lowered from −20° C. to −80° C.

Having now fully described this invention, it will be understood to those of ordinary skill in the art that the methods of the present invention can be carried out with a wide and equivalent range of conditions, formulations and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method for sterilizing a biological material that is sensitive to radiation, said method comprising irradiating said biological material and a combination of stabilizers comprising DMSO, mannitol and trehalose with gamma radiation for a time effective to sterilize said biological material at a rate effective to sterilize said biological material and to protect said biological material from said radiation.

2. The method according to claim 1, wherein the biological material contains a non-aqueous solvent.

3. The method according to claim 2, wherein said non-aqueous solvent is an organic solvent.

4. The method according to claim 2, wherein said non-aqueous solvent is selected from the group consisting of glycerol, ethanol, acetone and PPG.

5. The method according to claim 1, wherein said effective rate is not more than about 3.0 kGy/hour.

6. The method according to claim 1, wherein said effective rate is at least about 6.0 kGy/hour.

7. The method according to claim 1, wherein said biological material is maintained in a low oxygen atmosphere.

8. The method according to claim 1, wherein said biological material is maintained in a vacuum.

9. The method according to claim 1, wherein said biological material contains residual solvent.

10. The method according to claim 1, wherein at least one sensitizer is added to said biological material prior to said step of irradiating said biological material.

11. The method according to claim 1, wherein said biological material comprises at least one biological contaminant or pathogen selected from the group consisting of viruses, bacteria, yeasts, molds, fungi, parasites and prions.

12. The method according to claim 1, wherein said gamma irradiation is conducted at ambient temperature.

13. The method according to claim 1, wherein said gamma irradiation is conducted at a temperature below ambient temperature.

14. The method according to claim 1, wherein said biological material is selected from the group consisting of tissues, blood or blood components and proteins.

* * * * *